(12) United States Patent
Chudy et al.

(10) Patent No.: US 9,002,510 B2
(45) Date of Patent: *Apr. 7, 2015

(54) SYSTEM AND APPARATUS FOR ITEM MANAGEMENT

(71) Applicant: Chudy Group, LLC, Powers Lake, WI (US)

(72) Inventors: Duane S. Chudy, Lincolnshire, IL (US); Larry Montgomery, Butternut, WI (US); James T. Spernow, Gurnee, IL (US)

(73) Assignee: Chudy Group, LLC, Powers Lake, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/766,092

(22) Filed: Feb. 13, 2013

(65) Prior Publication Data

US 2013/0158706 A1    Jun. 20, 2013

Related U.S. Application Data

(63) Continuation of application No. 12/033,957, filed on Feb. 20, 2008, now Pat. No. 8,380,346.

(51) Int. Cl.
*G06F 17/00* (2006.01)
*G06F 19/00* (2011.01)
(Continued)

(52) U.S. Cl.
CPC ............ *G06F 17/00* (2013.01); *G06F 19/3462* (2013.01); *G06F 19/3475* (2013.01); *G06Q 50/22* (2013.01); *G07F 17/0092* (2013.01); *B65G 1/02* (2013.01)

(58) Field of Classification Search
CPC .................................................. G06F 19/3462

USPC ......... 700/242, 244, 231, 232, 236, 240, 243; 221/2, 5, 6
See application file for complete search history.

(56) References Cited

U.S. PATENT DOCUMENTS 4,685,271 A * 8/1987 Ringer et al. ................... 53/246
4,695,954 A   9/1987 Rose et al.
(Continued)

FOREIGN PATENT DOCUMENTS

CA    2628789       4/2008
EP    1433457 A    6/2004
(Continued)

OTHER PUBLICATIONS

Bastian Material Handling, LLC, Indianapolis, Indiana. <www.bastiansolutions.com>. Exacta Acculight "Pick to Light (PTL) Technology" from Bastian Material Handling. 6 pages. Date: Copyright 2008.

(Continued)

*Primary Examiner* — Michael K Collins
(74) *Attorney, Agent, or Firm* — Jansson Munger McKinley and Shape Ltd.

(57) ABSTRACT

Item-management systems, apparatus, and methods are described, preferably for management of items such as medicaments. In embodiments, an item-management system comprises a holder defining plural cells, a docking station configured to receive the holder, at least one indicator selectively-operable to indicate the holder cell into which an item is to be loaded, and at least one controller operable to selectively operate each at least one indicator to indicate the cell into which the item is to be received. In embodiments, indicators are provided on the holder. In other embodiments, the indicators may by on a guide associated with the docking station to assist the user in loading the holder. The contents of the loaded holder may be easily loaded, for example, into an automated dispensing machine for packaging and subsequent administration to a patient or for another use.

15 Claims, 24 Drawing Sheets

(51) Int. Cl.
  *G06Q 50/22*     (2012.01)
  *G07F 17/00*    (2006.01)
  *B65G 1/02*     (2006.01)

(56) References Cited

U.S. PATENT DOCUMENTS

| | | | |
|---|---|---|---|
| 4,763,810 A * | 8/1988 | Christiansen | 221/3 |
| 4,771,912 A * | 9/1988 | van Wingerden | 221/75 |
| 4,838,453 A * | 6/1989 | Luckstead | 221/2 |
| 5,408,443 A | 4/1995 | Weinberger | |
| 5,915,589 A * | 6/1999 | Lim | 221/3 |
| 6,021,392 A | 2/2000 | Lester et al. | |
| 6,021,918 A * | 2/2000 | Dumont et al. | 221/2 |
| 6,102,855 A | 8/2000 | Kehr et al. | |
| 6,170,699 B1 * | 1/2001 | Kim | 221/85 |
| 6,294,999 B1 | 9/2001 | Yarin et al. | |
| 6,338,007 B1 | 1/2002 | Broadfield et al. | |
| 6,349,848 B1 | 2/2002 | Uema et al. | |
| 6,457,611 B1 * | 10/2002 | Koehler | 222/462 |
| 6,581,356 B2 | 6/2003 | Kim | 53/154 |
| 6,658,322 B1 | 12/2003 | Frederick et al. | |
| 6,702,146 B2 * | 3/2004 | Varis | 221/3 |
| 6,705,487 B2 * | 3/2004 | Kim | 221/312 B |
| 6,762,681 B1 | 7/2004 | Danelski | |
| 6,779,663 B1 * | 8/2004 | Pocsi | 206/534 |
| 6,925,783 B1 * | 8/2005 | Pearson | 53/475 |
| 7,177,721 B2 | 2/2007 | Kirsch et al. | |
| 7,195,156 B2 | 3/2007 | Venema et al. | |
| 7,203,571 B2 | 4/2007 | Kirsch et al. | |
| 7,228,988 B2 | 6/2007 | Inamura | |
| 7,369,919 B2 | 5/2008 | Vonk et al. | |
| 7,472,526 B2 * | 1/2009 | Pearson | 53/473 |
| 7,848,846 B2 * | 12/2010 | Uema et al. | 700/243 |
| 7,856,794 B2 * | 12/2010 | Zieher | 53/246 |
| 7,922,037 B2 | 4/2011 | Ohmura et al. | |
| 7,971,414 B1 * | 7/2011 | McGonagle et al. | 53/246 |
| 8,380,346 B2 * | 2/2013 | Chudy et al. | 700/242 |
| 2003/0057231 A1 | 3/2003 | Kim | |
| 2004/0134043 A1 | 7/2004 | Uema et al. | |
| 2005/0145644 A1 | 7/2005 | Mori et al. | |
| 2006/0184271 A1 * | 8/2006 | Loveless | 700/231 |
| 2007/0073560 A1 | 3/2007 | Walker et al. | |
| 2009/0014461 A1 | 1/2009 | Omura et al. | |
| 2009/0120042 A1 * | 5/2009 | Zieher | 53/467 |
| 2009/0152291 A1 | 6/2009 | Ohmura et al. | |

FOREIGN PATENT DOCUMENTS

| | | |
|---|---|---|
| EP | 2093722 A1 | 8/2009 |
| JP | 2007209600 A | 8/2004 |
| JP | 2007297066 A | 11/2007 |
| WO | WO2004088463 | 10/2004 |
| WO | WO2007091375 A1 | 8/2007 |

OTHER PUBLICATIONS

Lighthouse Selection, LLC, Manchester, New Hampshire. <www.lighthouseselection.com>. web page. 2 pages. Date: Copyright 2006.

Innovative Picking Technologies, Inc., Ixonia, Wisconsin. <www.ipti.net>. "Econo-Pick." 2 pages. Date: Undated.

Warehouse Equipment, Inc., Elk Grove, Illinois. <www.weinet.com>. WEI Material Handling Solutions webpage. 1 page. Date: Copyright 2005.

Bastian Material Handling, LLC, Indianapolis, Indiana. <www.bastiansolutions.com>. "Controls and Automation Interfaces" brochure. 11 pages. Date: Undated.

Innovative Picking Technologies, Inc., Ixonia, Wisconsin. <www.ipti.net>. "Pick-Max 2" brochure. 5 pages. Date: Undated.

Photograph of medicament loading device not including medicaments. Date: 2007 and earlier.

Photograph of medicament loading device including medicaments. Date: 2007 and earlier.

European Search Report. EPO Application No. 09152723.4. Date: Jun. 16, 2009. 6 pages.

Tosho, Tokyo, Japan. "U2 Xana-4001U2" brochure. Date: Undated. 4 pages.

* cited by examiner

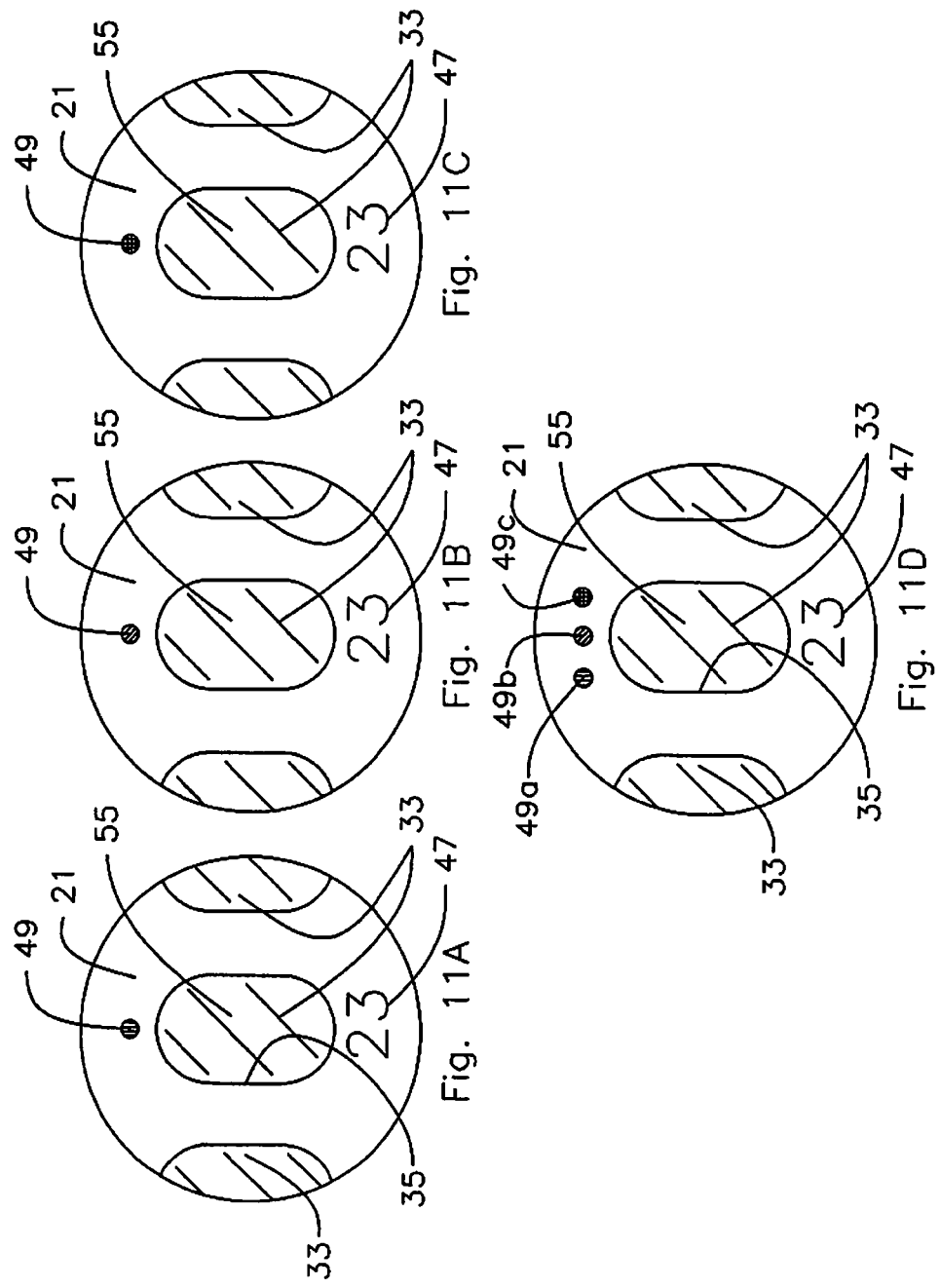

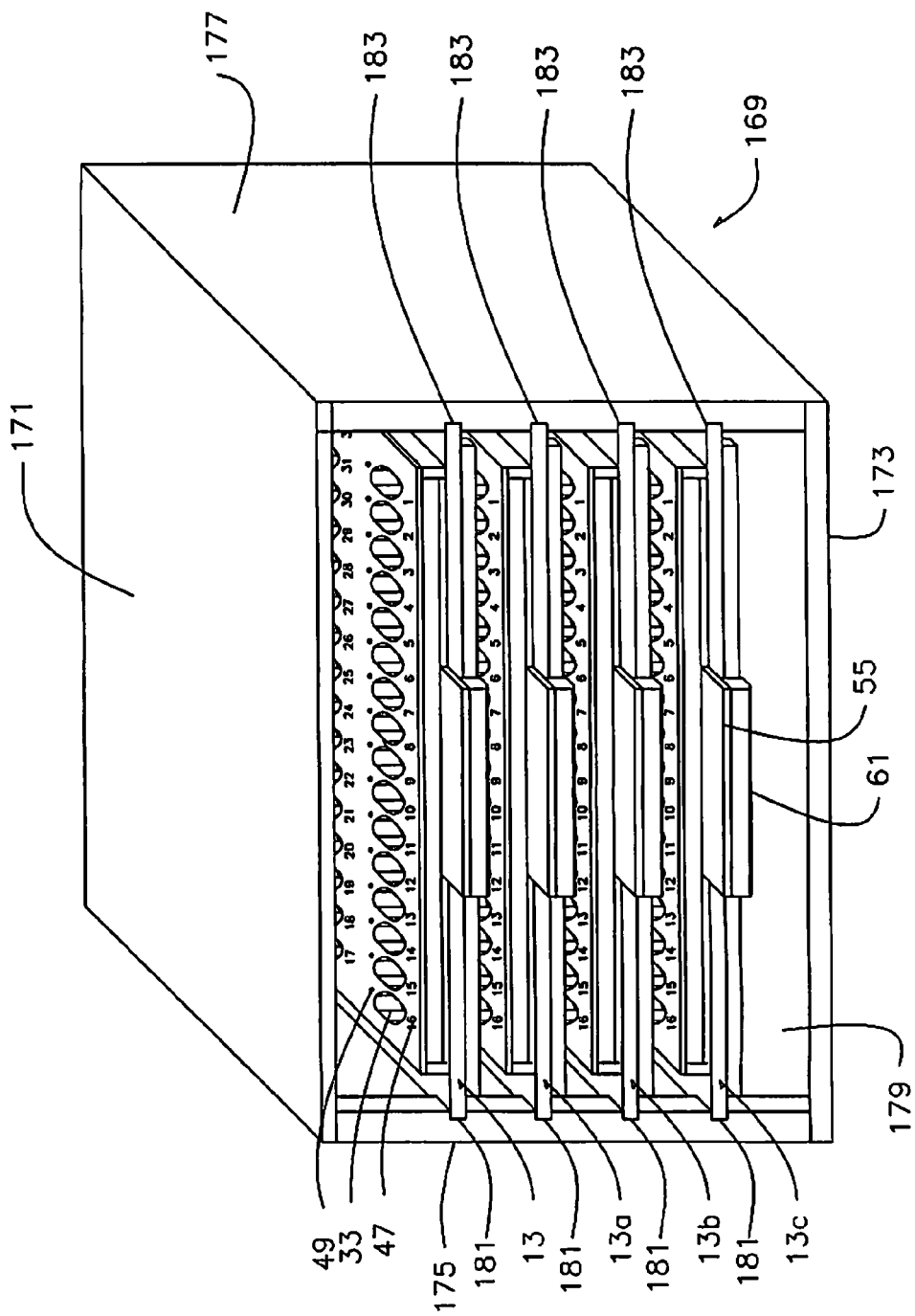

SYSTEM AND APPARATUS FOR ITEM MANAGEMENT

CROSS REFERENCE TO RELATED APPLICATION

This application is a continuation of U.S. patent application Ser. No. 12/033,957, filed Feb. 20, 2008, now U.S. Pat. No. 8,380,346, issued Feb. 19, 2013. U.S. patent application Ser. No. 12/033,957 is incorporated herein by reference in its entirety to provide continuity of disclosure.

FIELD

The field relates generally to item management and, more particularly, to item management providing for improved efficiency in item distribution.

BACKGROUND

Personnel involved in handling of items are routinely required to manage and organize the items for delivery to an appropriate user or process. An item as used herein, means or refers to a separate article, object, or product. Care is required to ensure that the correct item is delivered to the user or process. Examples of such item-management tasks involve handling of medicament or nutriceutical items ultimately intended for use by a patient, consumer, or other user. A medicament means or refers to a medication product while a nutriceutical can represent a dietary supplement which provides health or medical benefits. (e.g., a vitamin, a mineral, or a supplement.)

Items such as medicaments and nutriceuticals are provided in various physical forms, such as solid or substantially solid forms, granular forms, gel forms, and liquid forms. Solid or substantially solid medicament and nutriceutical items may be shaped into small solid tablets in the physical form of capsules, spheres, ovals, disks, multi-angles, squares, triangles, and ellipses. Gel, granular, or liquid-form items may be packaged in the form of small capsules and gel caps (for oral consumption), or ampules containing a liquid. Medicament and nutriceutical items may also be provided which differ in strength of the active chemical constituent. For example, a single medicament or nutriceutical item may be provided with a concentration of 1, 5, or 10 milligrams of the active chemical constituent.

One way in which the foregoing types of items are managed for delivery to the ultimate user is through automated dispensing machines. Automated dispensing machines are frequently utilized by pharmacies, hospitals, long-term care facilities, and others in the health-care field for purposes of automatically dispensing medications required to fulfill patient prescription orders and to dispense medicaments administered to patients in hospitals and long-term care facilities, such as nursing homes. Automated dispensing machines can also be used in retail distribution, such as to dispense nutriceutical or food items. Such automated dispensing machines are computer controlled to dispense an appropriate quantity of medicaments and, typically, to package the medicaments. And, automated dispensing machines can typically be programmed to dispense and package all medicaments required to fulfill all prescription orders and dispense requests for a given eight-hour work shift. The automated dispensing machine will proceed to automatically execute the instructions until all requested medicaments have been output.

Automated dispensing machines typically store and dispense a plurality of different medicament types. Medicaments which are frequently prescribed or utilized, referred to as "fast-moving" medicaments, are stored within the automated dispensing machines in large quantities as loose, bulk form items within cassettes, cells, canisters, magazines, racks, or other storage apparatus. A single medicament type is stored in each storage apparatus.

Medicaments which are less frequently prescribed or utilized are referred to as "slow-moving" medicaments. Medicament types which are infrequently required may be stored in the automated dispensing machine in what is referred to as an "exception storage apparatus," a type of storage apparatus which derives its name merely from being an alternative to the medicament storage apparatus used for the faster moving medicaments. Slow-moving medicaments could include medicament types with unusual chemical constituents or with unusual active-constituent concentrations. An exception storage apparatus stores small quantities of the less-frequently used medicaments which could not be efficiently stored in large bulk quantities. Unlike the cassettes, cells, canisters, magazines, racks, or other storage apparatus for the faster moving medicaments, more than one medicament type can be stored in a single exception storage apparatus.

An exception storage apparatus can be provided, for example, as a drawer, or as a tray-like device, which pulls out from the automated dispensing machine and which includes a plurality of medicament-holding cells, or compartments, for holding one medicament item or a small quantity of medicaments. In certain automated dispensing machine types, the cells of the exception storage apparatus are movable along a track. The cells can be indexed forward along the track toward an opening so that the cell contents fall serially (i.e., one-after-the-other) through a cell bottom opening for packaging by the machine. Any number of cells can be provided in the exception storage apparatus. For example, an exception storage apparatus could include 64 total cells grouped in four rows of 16 cells all movable along the track. More than one exception storage apparatus may be provided.

The exception storage apparatus offers the operator an opportunity to increase the range of dispensing options because more than one type of medicament can be stored in such storage apparatus. For example, the medicaments can be arranged in the exception storage apparatus to dispense medicaments for a particular patient according to the order in which the medicaments are to be taken by the patient (e.g., breakfast, lunch, and dinner) or can be loaded to meet the medicament requirements of more than one patient.

Upon activation, the automated dispensing machine automatically meters out from the appropriate storage apparatus the desired quantity of medicament(s) called for by the prescription order or dispense request. The medicament item or items are directed from the storage apparatus to the packaging apparatus by means of gravity through a chute or other guide apparatus, or by mechanical means such as an auger. The packaging device may then load the dispensed medicaments into one or more packages. The type of package utilized is based on the capability of the particular type of automated dispensing machine. By way of example only, automated dispensing machines may load the medicaments into containers such as vials, bottles, blister packages, or pouch packages. The medicament or medicaments, once packaged in the container type utilized by the automated dispensing machine, may then be delivered to the patient or other designated user.

Loading or replenishment of the cassettes, cells, canisters, or other storage apparatus for the fast moving medicaments is relatively easy. All that is required is placement of a loaded storage apparatus into the machine (e.g., in place of a depleted storage apparatus) or the pouring of a quantity of the bulk-form medicaments into a depleted storage apparatus.

However, loading or replenishment of the cells or compartments of the exception storage apparatus is more problematic because a human being must manually load or replenish the cells or compartments. In a pharmacy, hospital, or long-term care facility, the human is a pharmacy technician or a registered pharmacist. The technician or pharmacist must manually load the medicament items directly into the exception storage apparatus cells. Alternatively, the medicament items can be placed into the cells of a "loading device." A loading device is a device with cells or compartments that correspond to the cells of the exception storage apparatus. The loading device can be loaded at a workstation and carried to the automated dispensing machine so that the medicament contents of the loading device can be transferred into the appropriate cells of the exception storage device. By way of example only, a busy pharmacy might use dozens of different loading devices to load the exception storage apparatus during a given work shift.

The exception storage apparatus loading process is tedious and time consuming, irrespective of whether the medicament items are placed directly into the exception storage apparatus cells or are placed into the cells of a loading device for transfer to the exception storage apparatus. As can be appreciated, the loading process must be undertaken in a deliberate and considered manner to ensure that the correct medicament is placed in the correct cell or compartment. Placement of the correct medicament in the correct cell or compartment can be difficult because the cells or compartments of a typical exception storage apparatus or loading device are relatively small and are in close proximity to each other. The chance of an inadvertent error may be increased because certain medicaments have similar shapes, sizes, and appearances.

Typically, printed paper instructions are generated which direct the technician or pharmacist to place the required medicament into a designated cell or compartment. At a minimum, valuable time is required to follow the instructions. The instructions may require complex ordering of different medicament types among the cells raising the possibility, no mater how slight, that the wrong medicament could be placed in a cell or compartment. And, because the technician or pharmacist must take her eyes off the exception storage apparatus or loading device to read the instructions, and because the cells typically look alike, there is also a slight possibility that the wrong medicament item could be placed in the cell. And, since more than one loading device could be used by a pharmacy, there is a possibility, no matter how remote, that an incorrect loading device could be used to load the exception storage apparatus.

If a pharmacist is required to inspect a loading device or exception storage apparatus before use to verify that the medicaments were loaded correctly, then the pharmacist must essentially repeat the loading process to confirm that the correct medicament was received in the correct cell.

A skilled pharmacist's time is extremely valuable. Time spent loading an exception storage apparatus is time that could be spent counseling patients. And, an automated dispensing machine must typically be deactivated or taken "off line" in order to load the exception storage apparatus. Any time spent loading an exception storage apparatus can represent lost productive time in which the automated dispensing machine cannot be used to fulfill prescription orders or dispense requests, thereby decreasing efficiency and increasing costs to the operator.

Problems similar to those described for operators of automated medicament dispensing machines can exist for operators of other types of automated dispensing machines in which both fast and slow moving items must be dispensed from a single machine. For instance, the same issues would face the operator of an automated dispensing machine used to dispense nutriceutical products or other retail food products.

There is a need for an item-management system, apparatus and methods which would improve the item management and distribution process, which would facilitate more accurate item management and distribution, and which would reduce the time needed to manage items, thereby freeing personnel for other important tasks and improving the quality of care which can be offered.

SUMMARY

Item-management systems, apparatus and methods are described. The systems, apparatus, and methods facilitate management and organization of items, such as medicaments. The systems, apparatus, and methods may be used, for example, to ensure that the correct item is provided to a user or other process. The systems, apparatus, and methods are described in the preferred context of management of medicament-type items but can have application with respect to management of other items, such as nutriceuticals.

In embodiments, an item-management system comprises a holder having plural cells, a docking station to which the holder is docked, at least one indicator selectively-operable to indicate the cell of a docked holder into which an item is to be received, and at least one controller operable to selectively operate each at least one indicator to indicate the cell into which the item is to be received.

In embodiments, a holder for management of items comprises a body defining plural cells. Preferably, each cell has an inlet and an outlet. It is further preferred that at least one gate is mounted with respect to the body and each cell outlet. The preferred gate is movable between a first position in which the cell outlet is closed to receive an item in the cell and a second position in which the cell outlet is open to discharge the item from the cell. A preferred gate type is a shuttle member. Preferably, the shuttle member includes a pull permitting user operation of the shuttle member. In embodiments, the holder cells are in alignment with corresponding cells of an automated dispensing machine exception storage apparatus, thereby permitting rapid transfer of medicaments from the holder cells, preferably through the outlets, and to the automated dispensing machine.

At least one indicator proximate each cell is selectively operable to indicate the cell into which an item is to be received. The indicators can also be used for verification that the correct item was placed into the cell. Each at least one indicator provides visible information to the technician, pharmacist or other user, freeing personnel from reliance on written instructions regarding the medicament or other item to be placed in each holder cell. In embodiments, each at least one indicator is a lamp. Preferably, each lamp is a light-emitting diode, also known as an LED. In embodiments, a plural-lamp indicator consisting of more than one indicator can be provided proximate each cell, for example to provide different types of information. For example, each indicator may indicate the quantity or type of medicament to be placed in each cell. Plural indicators with colors that differ, or a single multi-colored indicator, lamp, or LED may be used, also to communicate useful information to the user.

In preferred embodiments, the indicators are associated with the holder. In other preferred embodiments, the indicators may be associated with a guide provided as part of the docking station. The preferred guide is located above a holder docked at the docking station and includes openings in registry with the holder cells. The indicators indicate which opening through which to place the medicament or other item to load the medicament or item into the appropriate holder cell.

In embodiments, a holder may be docked to a docking station by an electro-mechanical connection between mating contacts on the holder and docking station when a holder is docked. In other embodiments a holder may be docked to a docking station by a wireless connection with, or without, direct physical contact between the holder and docking station. Each connection type enables the selective indicator operation. A preferred holder body may include structure facilitating alignment of the holder and docking station for holder docking. In yet other embodiments, a holder may be directly connected to a controller, without a docking station. Preferred docking station embodiments may include a video display operably connected to the at least one controller and an input device (e.g., a keyboard and/or mouse) enabling a user to input information to the at least one controller. Preferably, the video display is operable to display information which indicates the cell into which each medicament is to be received.

Preferably, the at least one controller is operatively connected to each at least one indicator when the holder is docked at the docking station. It is preferred that the at least one controller comprises a computer including a set of instructions operable to selectively operate each at least one indicator. Most preferably, the at least one controller further includes a programmable logic controller operatively connected to the computer and the PLC selectively operates each at least one indicator. In embodiments, the instructions may be operable to selectively operate the indicators to control loading of a medicament into a cell for a patient or for a plurality of patients. The instructions may be operable to store information about the medicament loaded into each cell.

Methods for management of medicaments and items are shown and described herein.

BRIEF DESCRIPTION OF THE DRAWINGS

Exemplary item-management systems, apparatus, and methods may be understood by reference to the following description taken in conjunction with the accompanying drawings, in which like reference numerals identify like elements throughout the different views. For convenience and brevity, like reference numbers are used for like parts amongst the embodiments. The drawings are not necessarily to scale, emphasis instead being placed upon illustrating the principles of the invention. In the accompanying drawings:

FIGS. 11A-11C are enlarged fragmentary views of region 11 of FIGS. 3, 6, and 9 provided to illustrate an alternative indicator embodiment comprising a multi-colored lamp which may be used with the holders or guide of FIGS. 3, 6, and 9;

FIG. 11D is an enlarged fragmentary view of region 11 of FIGS. 3, 6, and 9 provided to illustrate a further alternative indicator embodiment comprising a tri-lamp indicator which may be used with the holders or guide of FIGS. 3, 6, and 9;

FIG. 13 is a perspective view of a storage cabinet including four representative holders temporarily stored therein;

FIG. 19A is an enlarged fragmentary view of a portion of the exemplary exception storage apparatus of FIG. 19;

FIGS. 21A-21C show an exemplary sequence for loading the contents of the holder into the exception tray.

Figure 1:
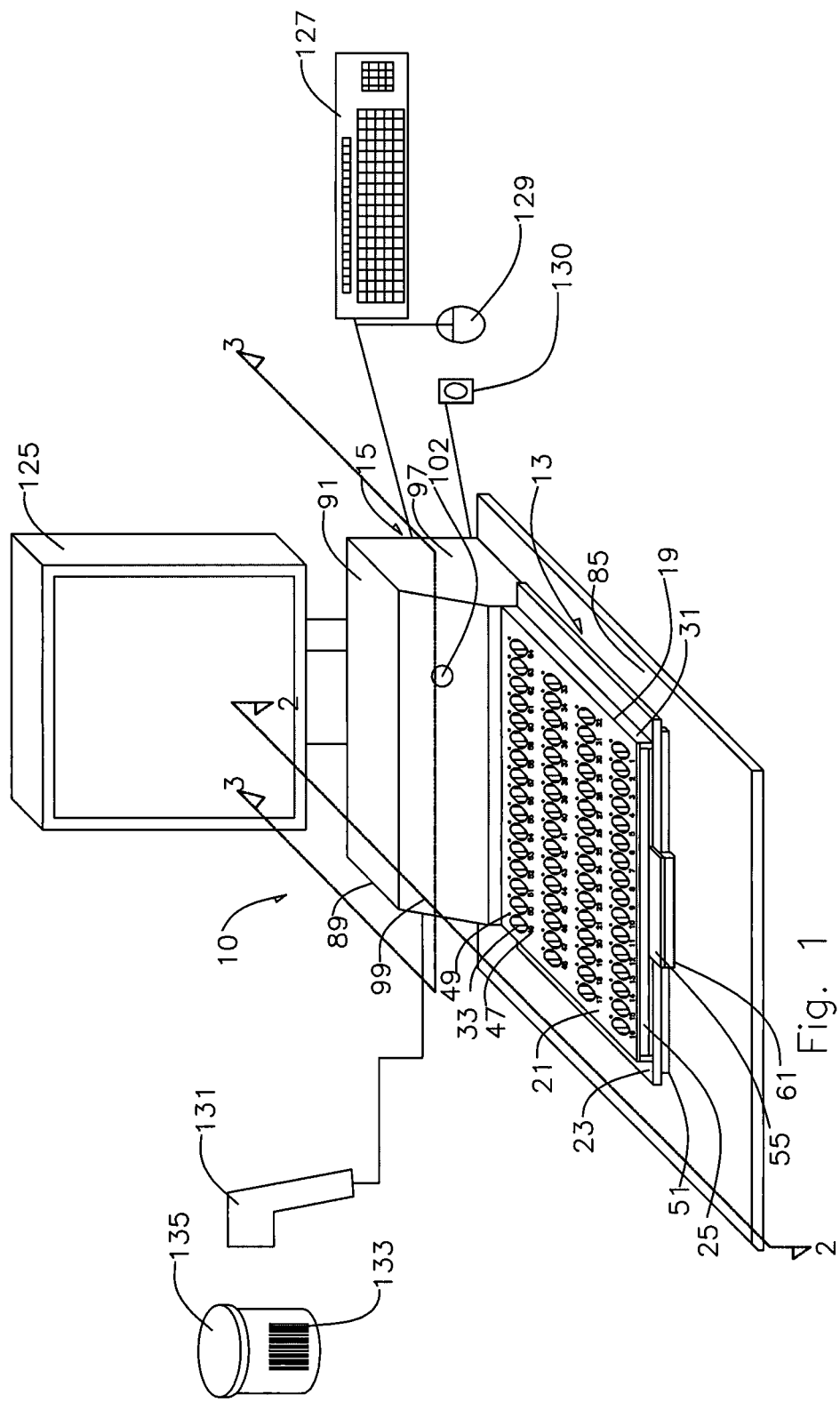
FIG. 1 is a perspective view of a representative holder docked at a docking station.

While the systems, apparatus, and methods are susceptible to various modifications and alternative forms, specific embodiments thereof have been shown by way of example in the drawings and are herein described in detail. It should be understood, however, that the description herein of specific embodiments and methods is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Referring first to FIGS. 1-9 and 12A, there are shown embodiments of an exemplary system 10 for management of items. The embodiments are described in the context of a preferred item-management system for management of medicament 11 items. System 10, preferably includes holder 13, docking station 15 to which holder 10 may be temporarily docked, and controller 17 which may include one or more controls capable of operating system 10. The term "at least one controller," therefore, means or refers to embodiments in which controller 17 includes one or more controller components. Controller 17 may include components internal and/or external to docking station 15. In a further exemplary system 10' (FIG. 12B), controller 17 is illustrated as being entirely within docking station 15. System 10 may be configured and arranged based on the needs of the pharmacy, hospital, long-term care facility or other operator. While it is envisioned that embodiments of system 10 or 10' will be utilized in the health-care industry, it should be understood that such systems and others may have application in fields outside of the health-care industry for dispensing of items other than medicaments 11.

Figure 5:
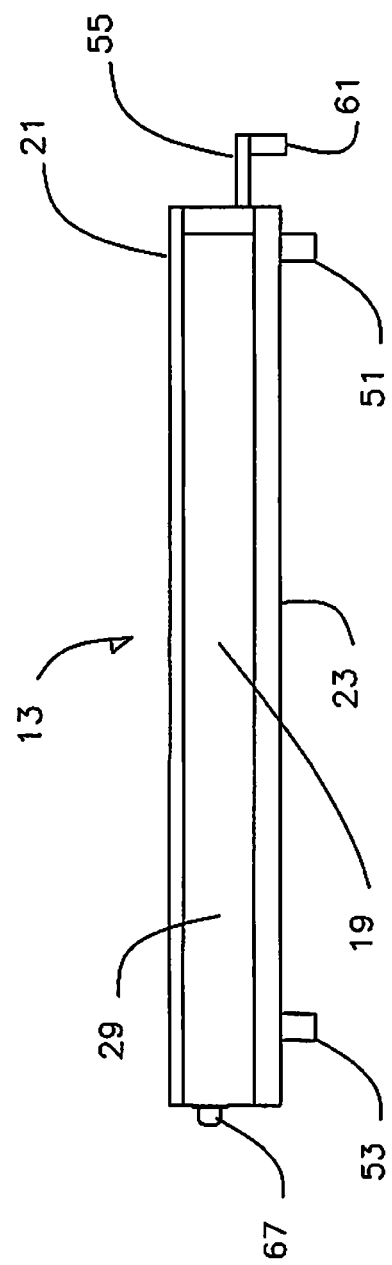
FIG. 5 is a left side elevation view of the representative holder of FIG. 1.
Figure 6:
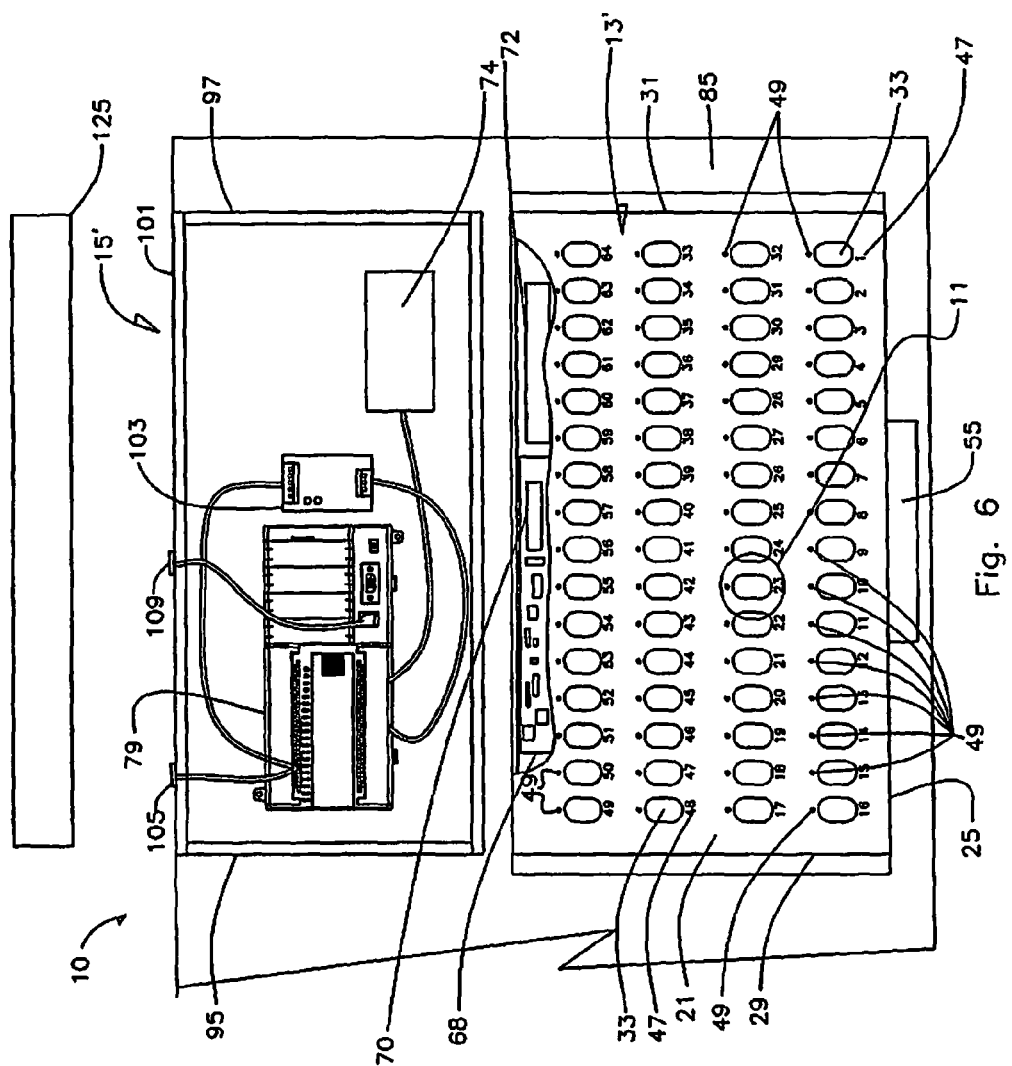
FIG. 6 is a schematic top sectional view of a representative wireless-type holder docked at a docking station taken along a section, such as section 3-3 of FIG. 1 with certain holder portions cut away to facilitate understanding.

Referring then to FIGS. 1-5, there is shown an exemplary holder 13 for managing and organizing medicaments. A further exemplary holder 13' is illustrated in FIG. 6. The word "holder" means or refers to apparatus which holds one or more items. Holder 13' is a wireless-type holder but is otherwise identical to holder 13. For simplicity and brevity, like reference numbers of holder 13 and docking station 15 are used to identify like parts of holder 13' and docking station 15' and the description of holder 13 and docking station 15 are incorporated by reference with respect to holder 13' and docking station 15'.

Exemplary holder 13, 13' has a tray-like appearance in that holder 13, 13' is a flat, shallow container used for carrying, holding, and organizing items which are preferably medicaments 11. However, other holder configurations may be utilized depending on the needs of the user.

Exemplary holder 13, 13' includes a body 19, a top and a bottom 21, 23, a front and a rear side 25, 27, and a left and a right side 29, 31. Holder 13, 13' further includes cells, of which cell 33 is representative. Each cell 33 is defined by a wall 35, of which wall 35 is representative. For purposes of simplicity and brevity, each cell 33 of holder 13, 13' is indicated by reference number 33 and each wall is indicated by reference number 35.

Each wall 35 defines a cell 33 upper opening, or inlet 37, and a cell lower opening, or outlet 39. As shown in the examples, the cell inlets 37 extend through, and are included in and along, the body top 21 while the cell outlets 39 extend through, and are included in and along, the body bottom 23. In the embodiments, medicaments 11 are loaded into each cell 33 through inlet 37 and are discharged from cell 33 through outlet 39 as described in detail below.

In the embodiments, each cell 33 is identical and, as noted, reference number 33 indicates each identical cell 33. However, it is possible that cells 33 of holder 13, 13' may have a structure which is not identical and which may differ depending on the needs of the user.

Referring to FIGS. 1-6 each exemplary holder 13, 13' shown includes sixty four total cells 33 organized into four rows of sixteen cells. In the examples, the organization of cells 33 is identical to the organization of cells 41 of exception storage apparatus 43 shown pulled out from automated dispensing machine 45 in FIGS. 18-21C. Exemplary holder 13, 13' is configured and arranged such that each cell 33 outlet 39 is in registry with (i.e., aligned with) a corresponding cell 41 of exception storage apparatus 43 permitting direct movement of medicaments 11 from holder 13, 13' into exception storage apparatus 43 as shown in the example of FIGS. 21A-21C.

Holder top 21 is preferably provided with human-readable indicia 47 identifying each cell 33. In the examples, indicia 47 is an integer from 1 to 64 proximate each cell 33. Other types of indicia 47 may be used, such as alpha-numeric indicia.

Holder 13, 13' further includes at least one indicator 49 for each cell 33, of which indicator 49 is representative. For purposes of simplicity and brevity, each indicator of holder 13, 13' is indicated by reference number 49. An indicator 49 is located on holder 13, 13' top side 21 next to each cell 33. Each indicator 49 could be located inside body 19 if body is translucent. One indicator 49 is provided for each cell 33 for a total of sixty four indicators 49 in these examples. Each indicator 49 may be a visible indicator in the form of a selectively-operable lamp (i.e., an artificial light source). Energizing of each lamp-type indicator 49 indicates the cell 33 into which the medicament 11 or other item is to be loaded. Preferably, each indicator 49 is a light-emitting diode (LED), although it is envisioned that other types of lamp-type indicators 49 may be used.

Controller 17 is operable to selectively operate each indicator 49 when holder 13 is docked at docking station 15. Selective operation of an indicator 49 proximate to a cell 33 prompts the technician or pharmacist to place each medicament 11 into the cell 33 associated with the activated indicator 49 or indicators 49. Collectively, the indicators 49 comprise a type of pick-to-light system. Thus, if a medicament 11 is to be loaded in the cells 33 designated by human-readable indicia 47 as cells 1, 3, 6, 9, 12, 15, 18, 21, 24, and 27, each of the indicators 49 next to such cells 33 may be activated communicating to the technician or pharmacist the specific cells 33 which should contain that medicament 11. Use of a pick-to-light system of indicators 49 advantageously communicates information to the technician or pharmacist without resort to a set of written instructions. A pick-to-light system is far superior to written instructions because the person responsible for loading or verification of holder 13, 13' need not take his or her eyes off of holder 13, 13' to read the instructions thereby increasing accuracy and reducing the time required to load or verify the medicaments 11 that should be in the holder 13, 13'.

As illustrated in yet a further embodiment illustrated in FIGS. 11A, 11B, and 11C, indicator 49 could comprise a single multi-colored indicator 49 for each cell 33. For example a multi-colored LED lamp could be used as indicator 49. As is known, changing the voltage to a multi-colored LED or selectively activating one of plural LED anodes causes the LED to emit a different color as represented in FIGS. 11A-11C. Each different color can be used to communicate a different type of information to the technician loading the holder 13, 13'. For example, a red color signal from indicator 49 (FIG. 11A) could indicate that one medicament 11 is to be loaded into that cell 33. A green-color signal from indicator 49 (FIG. 11B) could indicate that more than one medicament 11 is to be loaded in that cell 33. A yellow-color signal from indicator 49 (FIG. 11C) could indicate that a half-size medicament is to be loaded in that cell 33.

A further indicator 49 embodiment is illustrated in FIG. 11D. In the example of FIG. 11D, a plural-lamp indicator 49 could be provided for each cell 33 for purposes of communicating information to the technician or pharmacist. In FIG. 11D, a plural-lamp indicator 49 consisting of three lamps is provided adjacent each cell 33. Any number of lamps could be used. Each lamp of indicator 49 could, for example, consist of an LED lamp of a different color, such as red 49a, green 49b, or yellow 49c. Each color could indicate a different type of information as described in connection with the multi-colored LED example of FIGS. 11A-11C. Energizing of only the red-color indicator 49a could indicate that one medicament 11 is to be loaded into that cell 33. Energizing of only the green-color indicator 49b could indicate that more than one medicament 11 is to be loaded in that cell 33. Energizing of only the yellow-color indicator 49c could indicate that a half-size medicament is to be loaded in that cell 33. Alternatively, the lamps may all be of the same color and the number of activated indicator lamps 49 proximate each cell 33 could indicate the quantity of medicaments to be placed in each cell 33. Alternatively, the indicator 49 could have a blink pattern indicating the medicament 11 to be loaded into the cell 33. A constant blink could indicate that one medicament 11 is to be loaded into the cell, two blinks could indicate that more than one medicament 11 is to be loaded in that cell 33, and three blinks could indicate that a half-size medicament is to be loaded in that cell 33. Operation of the indicators 49 as described can also be used for verification of medicaments received in each cell 33.

Holder 13, 13' further includes a pair of legs 51, 53 depending from holder 13, 13' bottom side 23. Legs 51, 53 may be provided to support holder 13 on a surface (such as counter top 85). Referring to FIGS. 1 and 5, bottom side 23 may extend outwardly from holder sides 29, 31 for a purpose described below.

Referring to FIGS. 1-6 and 21A-21C, exemplary holder 13, 13' further includes a planar shuttle member 55 positioned in planar track 57 in holder proximate each cell 33 outlet 39. Shuttle member 55 includes openings 59 and a pull 61 which permits the technician or pharmacist to grasp shuttle member 55 with his or her hand and to pull or push shuttle member 55.

In the example, shuttle member 55 is movable between a first position in which shuttle member 55 covers and closes each cell 33 outlet 39 as shown in FIG. 21A and a further position in which the shuttle member 55 openings 59 are in alignment with each cell 33 outlet 39, thereby opening each cell outlet 39 permitting medicaments 11 to drop from each cell 33 into a corresponding cell of exception storage apparatus 43 as shown in FIG. 21C. The first position of shuttle member 55 is referred to herein as a "cell-closed position" and the further position of shuttle member 55 is referred to herein as a "cell-opened position." In between these positions, the cells 33 are partially open permitting medicaments to start to fall from cells 33 as shown in FIG. 21B.

In the embodiments, shuttle member 55 serves as a gate, opening and closing each cell 33 as shuttle member 55 moves between the cell-closed (FIG. 21A) and cell-opened positions (FIG. 21C). Shuttle member 55 thereby blocks each cell outlet 39 in the cell-closed position permitting a medicament 11 to be loaded into each cell 33 for organizing and storage and further opens each cell outlet 39 permitting each medicament 11 to be discharged from holder 13, 13' for loading into exception storage apparatus 43 as described below.

Figure 3:
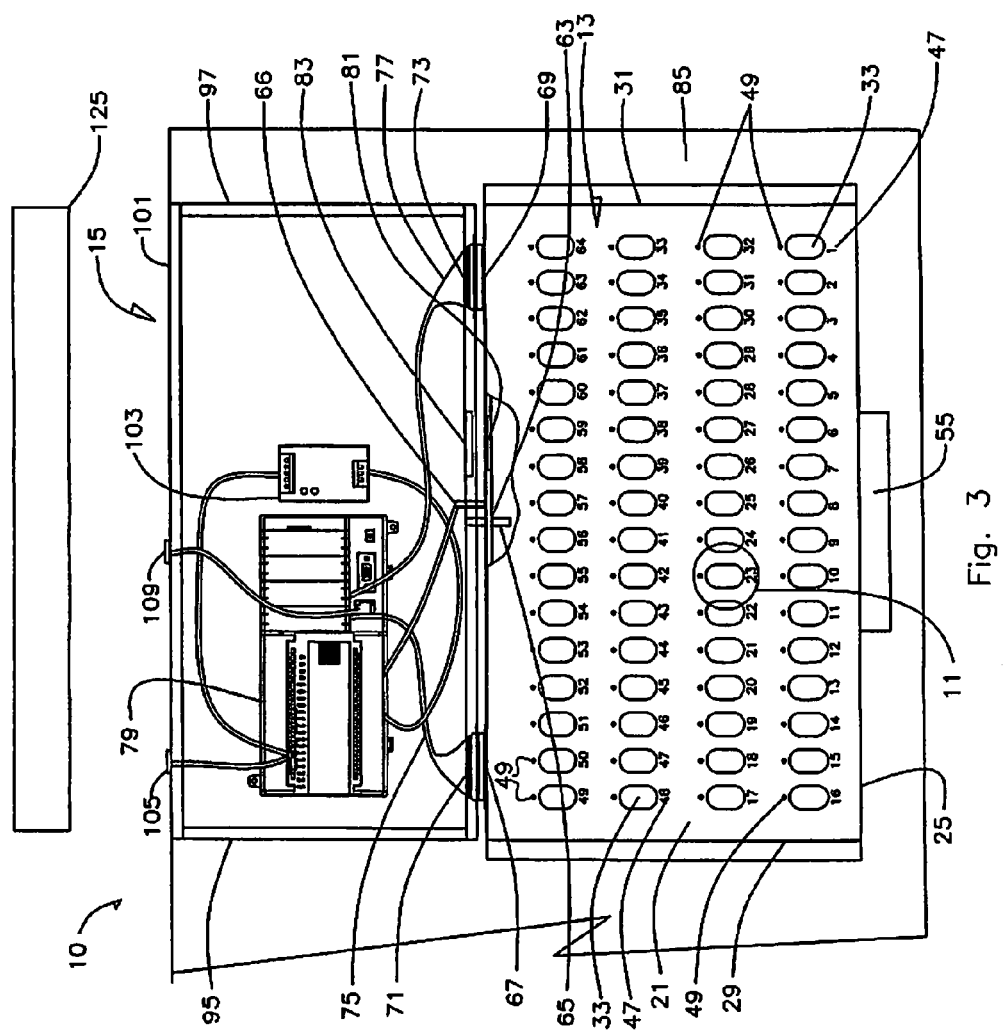
FIG. 3 is a schematic top sectional view of a representative holder docked at a docking station taken along section 3-3 of FIG. 1 with certain holder portions cut away to facilitate understanding.
Figure 4:
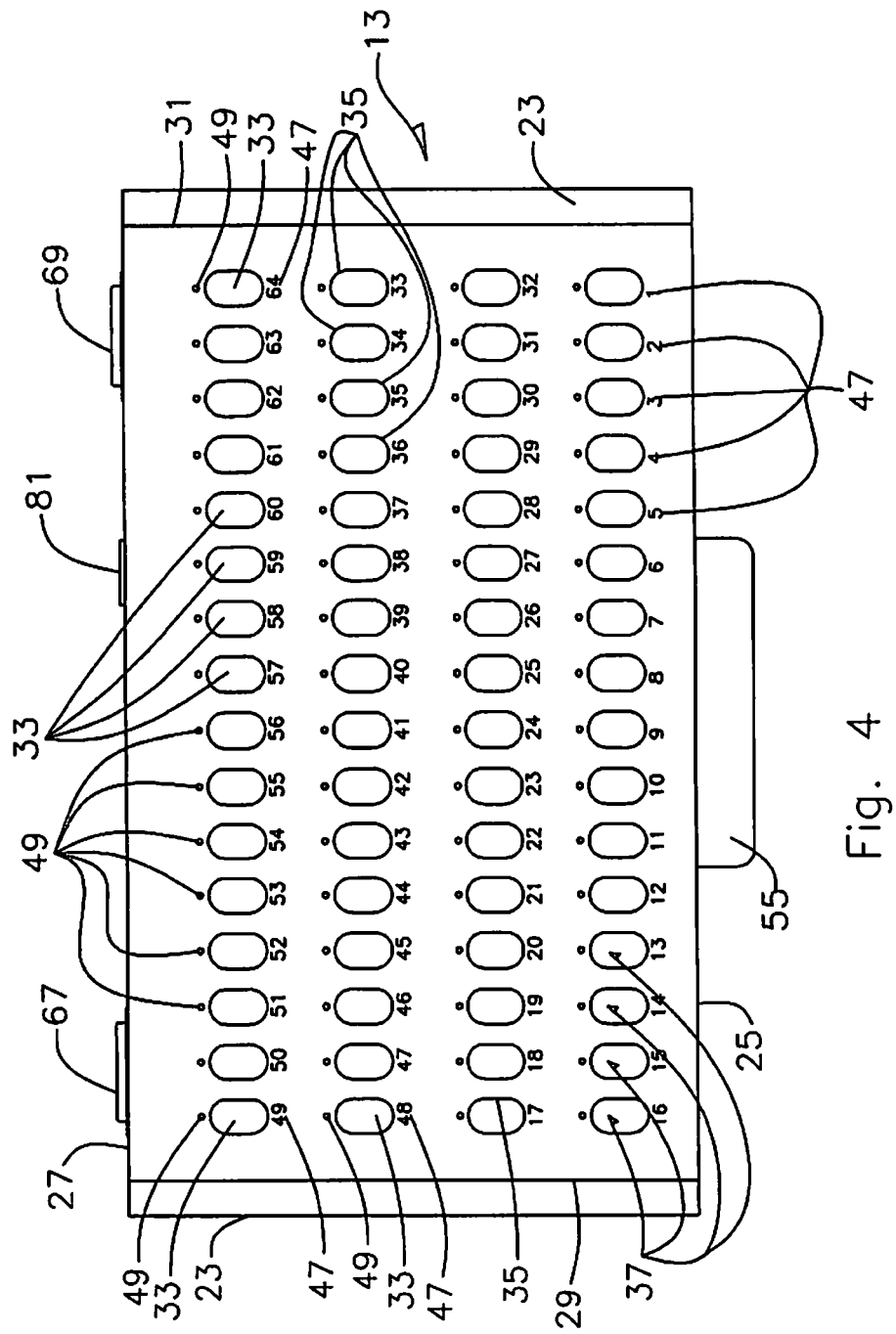
FIG. 4 is a top side view of the representative holder of FIG. 1.

Referring to FIG. 3, holder 13 and docking station 15 may include structure configured to enable or facilitate docking of holder 13 with docking station 15. In the embodiment, holder 13 is provided with a female alignment pin receiver 63 and docking station 15 is provided with a male alignment pin 65 which is inserted into and seated in receiver 63 when holder 13 is docked with docking station 15. The mechanical inter-connection of receiver 63 and pin 65 properly locates holder 13 at docking station 15. A contact-switch-type proximity detector 66 may be provided to indicate to controller 17 that holder 13 is properly docked at docking station 15. Holder 13' and docking station 15' may be provided with receiver 63, pin 65, and detector 66.

FIGS. 1-5 and FIG. 6 are provided to show exemplary types of connections between a holder and a docking station. Referring first to FIGS. 1-5, an exemplary electro-mechanical connection between holder 13 and docking station 15 is shown. In the example, holder 13 body 19 is provided with a pair of electrical contacts 67, 69 permitting control over operation of indicators 49 through docking station 15 and controller 17. Two contacts 67, 69 are not required as any number of contacts will suffice. When holder 13 is properly docked with docking station 15, contacts 67, 69 are brought into operable connection with corresponding contacts 71, 73 on docking station. Contacts 71, 73 are connected by suitable electrical conductors 75, 77 to programmable logic controller 79 of controller 17. Contacts 67, 69 are operably connected to indicators 49 through appropriate conductors (not shown) permitting selective energizing and operation of indicators 49 to indicate the cell 33 into which each medicament 11 is to be loaded. Examples of representative contacts 67, 69, 71, 73 for a holder 13 with sixty four indicators 49 are Amplimite™ 37 position, size 4 HD-20 male and female contacts available from Tyco Electronics of Harrisburg, Pa.

Referring now to FIG. 6, the holder 13' embodiment shown therein includes structure enabling wireless connection between holder 13', docking station 15,' and controller 17. Holder 13' includes a control circuit board 68, with a wireless transmitter/receiver 70 powered by a battery 72 associated with holder 13'. Board 68 is operably connected to indicators 49 through appropriate conductors (not shown) permitting selective energizing and operation of indicators 49 to indicate the cell 33 into which each medicament 11 is to be loaded or to permit verification of medicaments 11 received in cells 33. Transmitter/receiver 70 sends and receives signals with docking station 15' transmitter/receiver 74 permitting selective operation of indicators 49 through docking station 15' and controller 17.

In the examples of FIGS. 1-5 and FIG. 6, exemplary holder 13, 13' and docking station 15, 15' are provided with apparatus 81, 83 for uniquely identifying holder 13, 13' to docking station 15, 15' and system 10 or 10' as shown schematically in FIG. 3. Positive identification of holder 13, 13' enables the user to precisely control loading of appropriate medicaments 11 into holder 13 and 13' permits the user to maintain more accurate records of medicaments 11 which have been dispensed. In such embodiments, holder 13, 13' may include an identification element 81 and docking station 15, 15' may include an identification element detector 83 as shown in FIG. 3. The identifier element 81 may, for example, consist of a radio frequency identification tag (RFID) and the detector 83 may be an RFID tag reader (i.e., an interrogator) on docking station 15. The exemplary RFID tag 81 may be re-writable or read-only, as desired. Exemplary RFID reader 83 provided on docking station 15, 15' detects information embedded on the RFID tag 81. Information embedded in RFID tag 81 identifying holder 13, 13' may be used by system 10, 10' to control the medicament-dispensing process.

Figure 19:
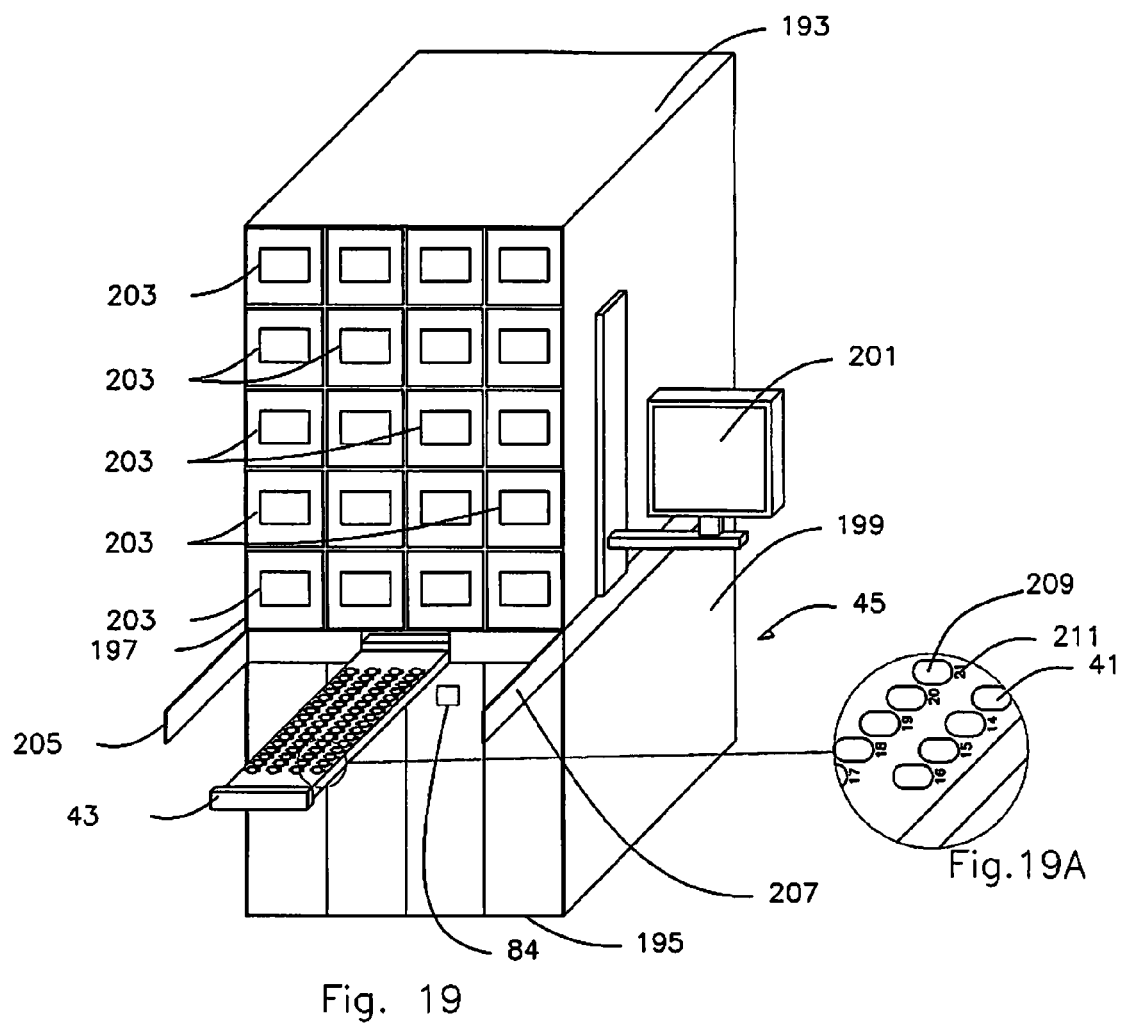
FIG. 19 is a perspective view of the exemplary automated medicament dispensing machine of FIG. 18, but with one exemplary exception storage apparatus in an outwardly-extended position ready to receive medicaments.
Figure 20:
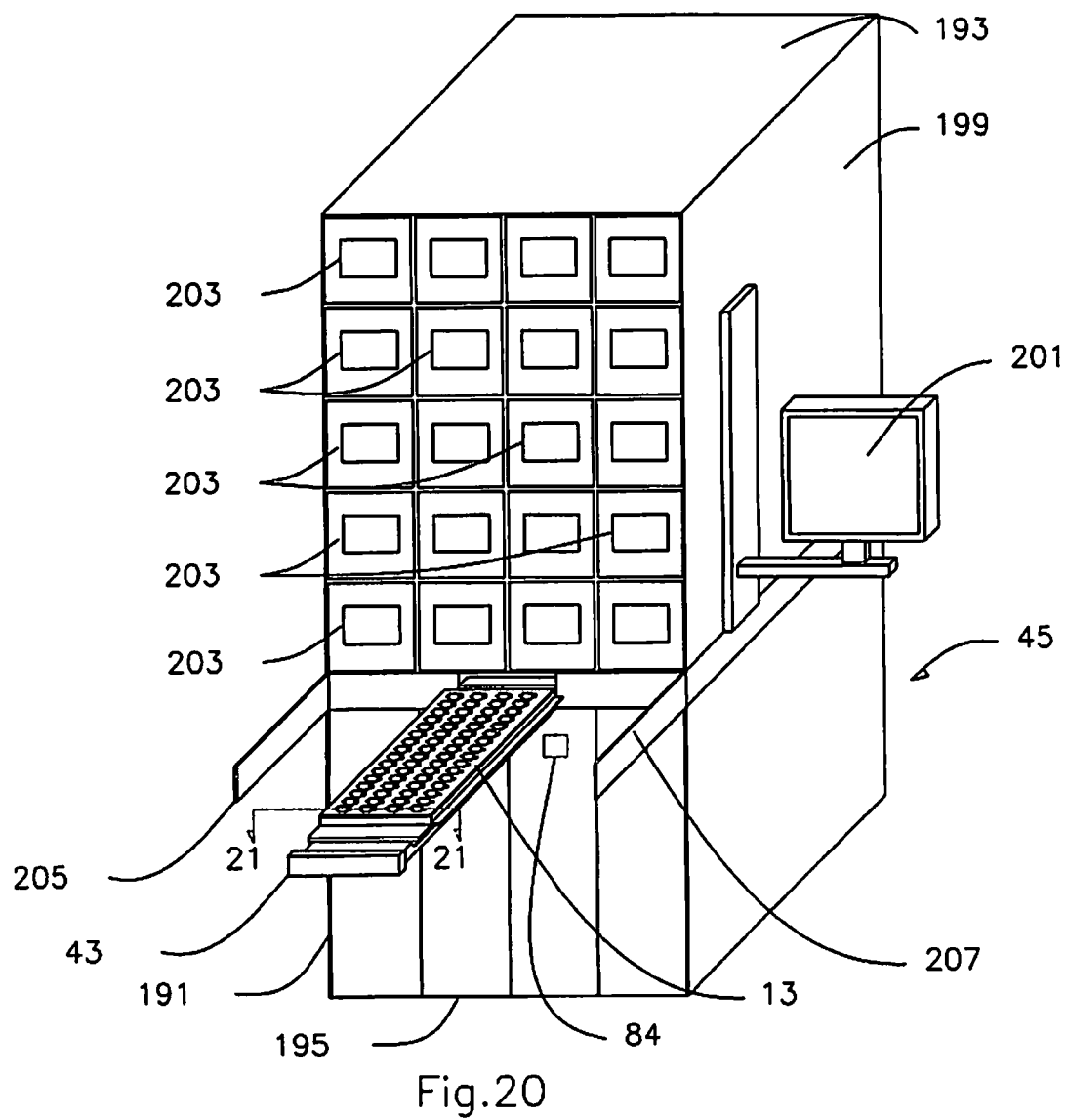
FIG. 20 is a perspective view of the exemplary automated medicament dispensing machine of FIGS. 18 and 19 but with the representative holder of FIGS. 1-10 positioned on the exemplary exception storage apparatus.
Figure 21A:
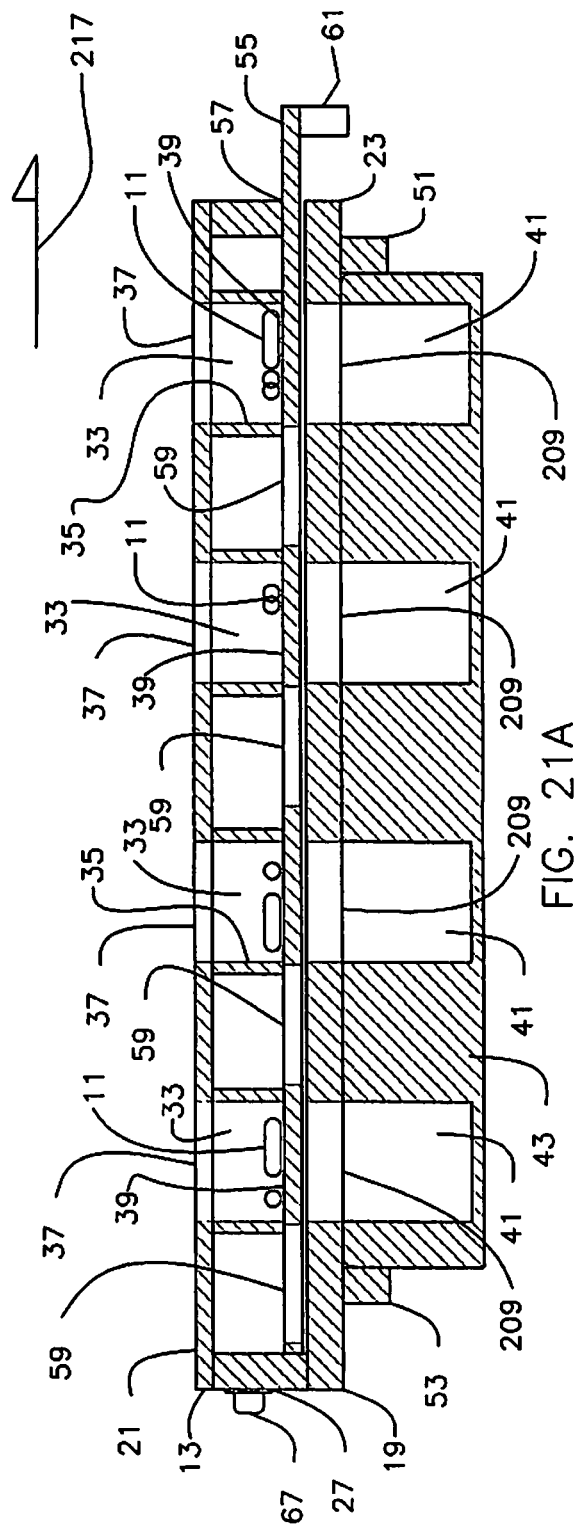
FIGS. 21A-21C are schematic side sectional views of the representative holder of FIGS. 1-5 and exception storage apparatus of FIGS. 19-20 taken along section 21-21 of FIG. 20.
Figure 21B:
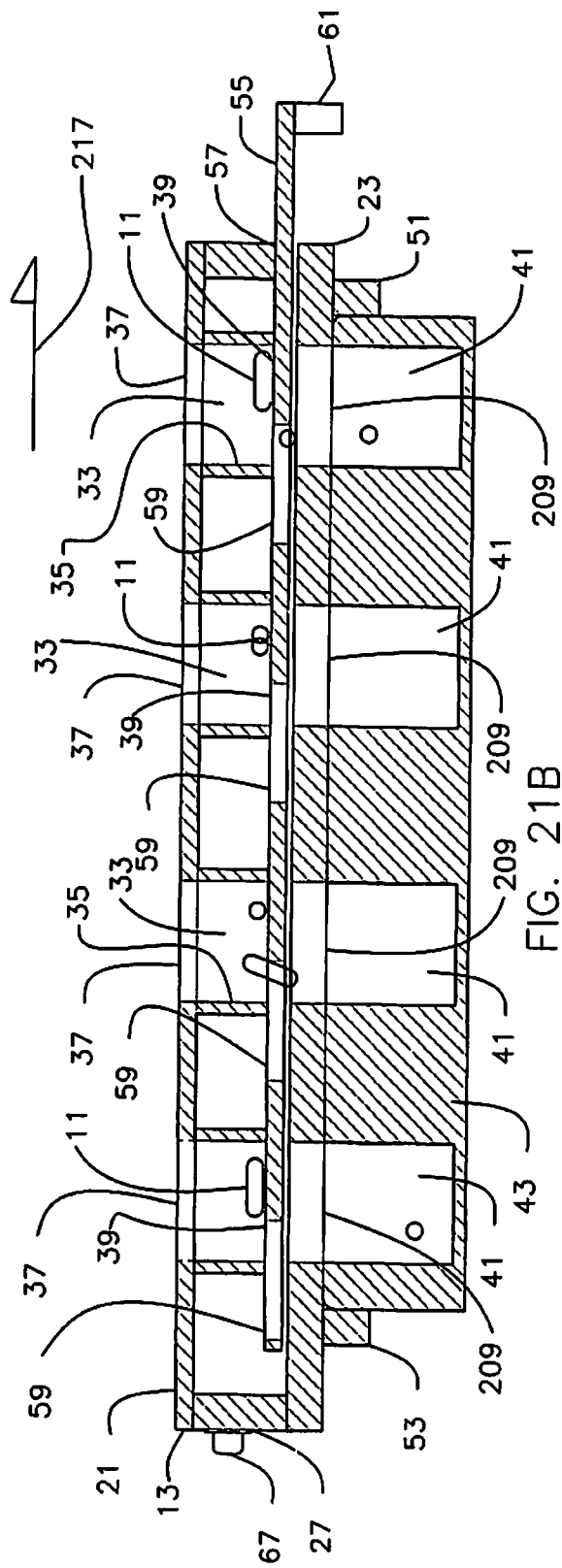
Figure 21C:
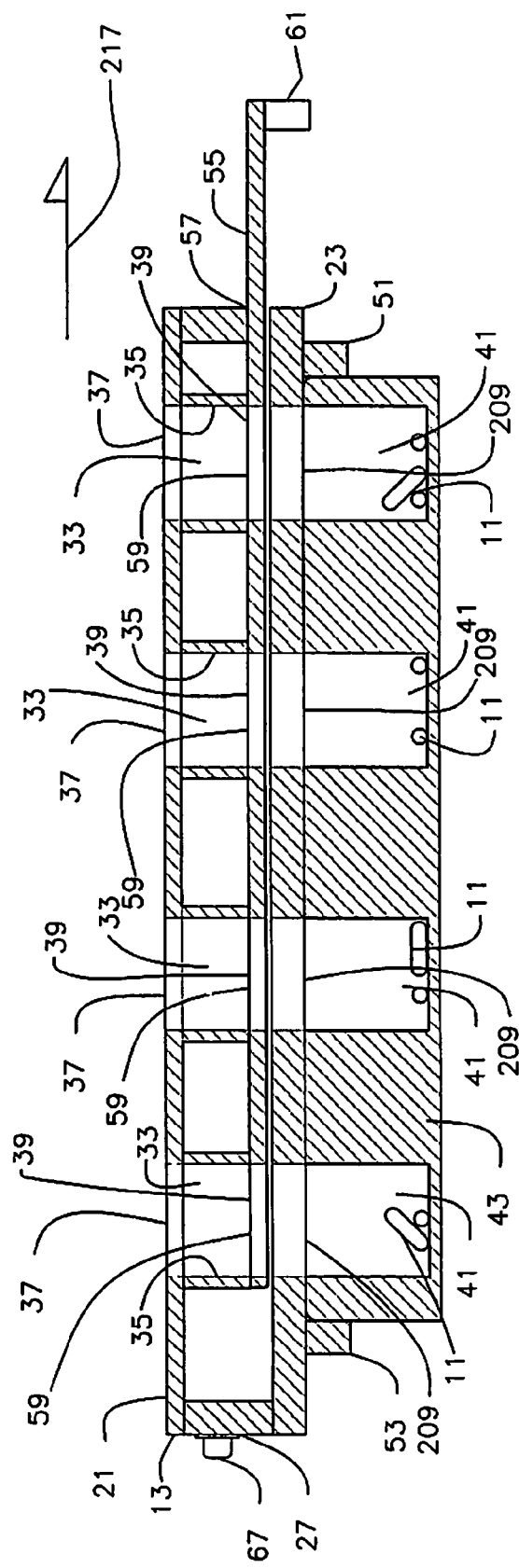

An identification element detector 84 may be provided on automated dispensing machine 45 (FIGS. 19, 20). In the example utilizing RFID tags, detector 84 may comprise an RFID reader. If the correct holder 13, 13' identification element 81 is detected by detector 84, the technician or pharmacist is prompted to transfer medicaments 11 from holder 13, 13' to exception storage apparatus 43. Conversely, if an incorrect holder identification element 81 is detected by detector 84, the technician or pharmacist is prompted to not load the exception storage apparatus 43.

Holder 13, 13' may be made of any suitable material or combination of materials. Preferably, body 19 is made of plastic material construction for reasons of ease of manufacture, low weight, ease of cleaning, and cost. Indicators 49 are preferably LED-type lamps but may comprise other types of visible indicators.

Referring next to FIGS. 1-3, and 6 there are shown embodiments of docking stations 15, 15' capable of use with a respective exemplary holder 13, 13'. Each docking station 15, 15' may be placed on a counter top 85, such as the counter top 85 at a workstation in a pharmacy, long-term care facility, hospital, or other facility. A mounting bracket 87 may be provided to mechanically secure docking station 15, 15' to counter top 85.

Each exemplary docking station 15, 15' preferably includes housing 89 including top and bottom walls 91, 93, left and right side walls 95, 97 and front and rear walls 99, 101. Indicator 102 is provided on front wall 99. Indicator 102 is preferably an LED lamp which is activated if a holder 13 is properly docked at docking station 15, 15' and is recognized as an authorized holder 13 by system 10, 10' by means of identifier element 81.

In the embodiments of FIGS. 1-3 and 6, housing 89 encloses a programmable logic controller (PLC) 79 and a power supply 103. In such embodiments, PLC 79 is a component of controller 17. Power-supply port 105 is provided for connection to a suitable 120 Volt electrical power source by means of an electrical cord (not shown) to supply electrical power to PLC 79. PLC 79 includes instructions permitting selective closing and opening of relays within PLC 79 corresponding to the indicator(s) 49 of holder 13, 13' which are to be selectively operated to indicate the cell 33 into which each medicament 11 is to be placed. Power supply 103 preferably provides 5 Volt DC power to selected ones of LED-type indicators 49 once the appropriate relays of PLC 79 are selectively closed, thereby providing selective energizing and operation of indicators 49. In embodiments utilizing a multi-color LED-type indicator 49 (FIGS. 11A-11C) PLC 79 may also regulate the voltage to each indicator 49 or selectively energize the anodes to change the color emitted by the multi-colored LED. In wireless holder embodiments 13', control circuit board 68 (e.g., a controller on board 68) activates indicator 49 responsive to signals generated by PLC 79 to transmitter/receiver 74. An exemplary PLC 79 suitable for use as a component of controller 17 is a Model 06 Koyo Electronics PLC available from Automation Direct, Inc. of Cumming, Ga.

Figure 12B:
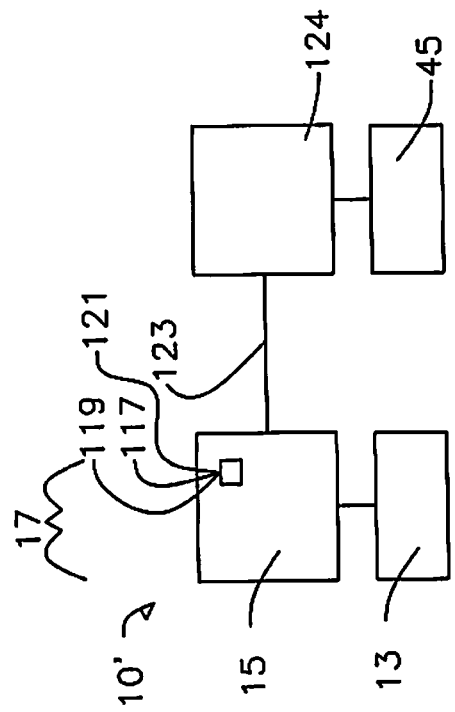
FIG. 12B is a schematic illustration of a further exemplary system including a docking station and computer internal to the docking station.
Figure 12A:
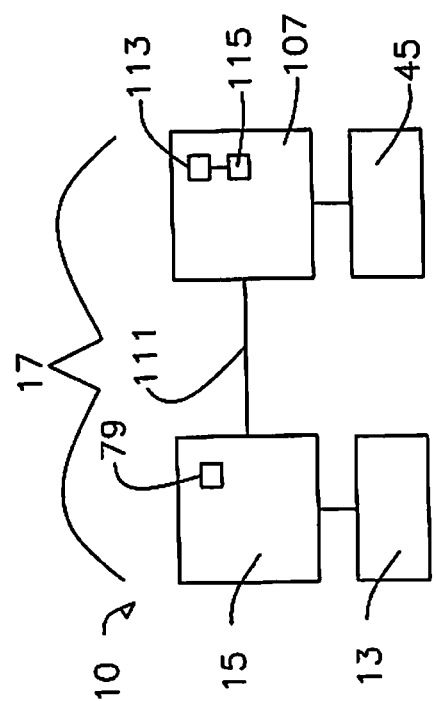
FIG. 12A is a schematic illustration of an exemplary system including a docking station and computer external to the docking station.

Referring to the embodiment of FIG. 12A, system 10 may include a server 107 operably connected to PLC 79 via data port 109 and communication link 111. In the embodiment, controller 17 includes both PLC 79 and server 107 operatively connected thereto. Server 107 may include memory 113 with a program of instructions 115 residing in memory 113. Server 107 is representative of any data management system operated by a pharmacy, hospital, long-term care facility, or other operator for purposes of managing information related to dispensing of medicaments 11. Communication link 111 may be any link capable of transmitting data and other information. Link 111 may, for example, comprise a dedicated land line, wireless link, ethernet, internet, intranet, local area network (LAN), or other suitable connection enabling data transmission between PLC 79 and server 107. Server 107 is preferably an off-the-shelf computer representative of any suitable data-management controller. It is envisioned that holder 13 can be connected directly to server 107 without a docking station 15, for example through a suitable communication link.

In a further illustrative embodiment represented by FIG. 12B, system 10' includes an on-board computer 117 within docking station 15, 15' housing 89 and computer 117 serves as controller 17. Computer 117 includes a program of instructions 119 residing in memory 121 which are operable to selectively energize and operate the indicators 49 to indicate the cell 33 into which one or more medicament(s) is/are to be placed. In this embodiment, computer 117 is linked to automated dispensing machine 45 via communication link 123 and server 124. Communication link 123 may be of the type as described previously in connection with link 111 and server may be a pharmacy information system server provided to manage pharmacy workflow generally. Overall activation of indicators 49 is provided by computer 117 in this example. System 10' is otherwise identical to system 10 and the description of system 10 is incorporated by reference with respect to system 10'.

Each docking station 15, 15' further preferably includes a video display 125, keyboard 127, and mouse 129 permitting a technician or pharmacist to input and receive information from server 107 or computer 117 of controller 17. A biometric identification device 130 may be provided to permit the technician or pharmacist to be identified to the system 10 or 10', particularly when logging on to the system. The biometric device 130 may be a fingerprint reader, retina scanner, or other suitable device. A bar code scanner 131 is preferably operably connected to controller 17. Video display 125 is preferably a touch screen display permitting a technician to input information to controller 17 by simply touching her finger on a desired portion of the display 125. Bar code scanner 131 may be any off-the-shelf scanner capable of reading a bar code 133 on a container 135 provided to hold medicaments 11. Keyboard 127 may be an off-the-shelf QWERTY-type keyboard 127 permitting a technician to input information to controller 17 and system 10, 10'.

FIGS. 7, 8, 9, and 10 illustrate a further holder 13" and docking station 15" embodiment suitable for use with an item-management system, such as system 10 or 10'. For simplicity and brevity, like reference numbers of holders 13, 13' and docking stations 15, 15' are used to identify like parts of holder 13" and docking station 15" and the description of holders 13, 13' and docking stations 15, 15' are incorporated by reference with respect to holder 13" and docking station 15". The embodiment of FIGS. 7-10 differs from the embodiments of FIGS. 1-6 because the indicator or indicators 49 which are selectively-operable to indicate the holder cell 33 into which an item is to be loaded are located on a guide 136 associated with docking station 15". Use of guide 136 with indicators 49 located thereon enables use of the item-management system with a holder 13" which does not include indicators 49 thereon, typical of holders presently in use.

Referring further to FIGS. 7-10, holder 13" includes body 19, top and bottom sides 21, 23, sides 25-31, cells 33 (including inlet and outlet openings 37, 39), legs 51, 53, shuttle member 55. An identification element 81 of the type previously described is preferably provided on body 19. An alignment pin receiver 63 may be provided to receive pin 65 of docking station 15" to position holder 13" at docking station 15". Exemplary docking station 15" includes detector 83, housing 89 with walls 91-101, lamp 102, power supply 103, and ports 105, 109, and is provided with a video display 125, keyboard 127, mouse 129, biometric identification device 130, and bar code scanner 131 for the purposes described in connection with docking stations 15, 15'.

Docking station 15" includes a guide 136 attached to housing front wall 99. Guide 136 is preferably a planar member located in a plane above a holder 13" docked at docking station 15" beneath guide 136. Guide 136 is provided with openings, each of which is identified by reference number 138 for brevity. In the example, guide 136 is provided with 64 total openings 138 grouped in four rows of openings 138. This opening 138 pattern is identical to the pattern of cells 33 in holder 13". This opening 138 pattern is such that the openings 138 in guide 136 are in registry and alignment with the corresponding cells 33 of holder 13" when holder 13" is docked at docking station 15". This arrangement allows a technician to rapidly and accurately load each cell 33 of holder 13" by inserting a medicament through the appropriate opening 138 in guide and into the corresponding cell 33 during holder 13" loading.

Indicators 49 on guide 136 are proximate each opening 138 to indicate to the technician, upon activation, which opening 138 a medicament 11 or other item is to be inserted. Indicators 49 may, for example, be a single lamp (preferably an LED) as illustrated in FIGS. 1, 3-4, 6-7, and 9, a multi-colored LED as illustrated in FIGS. 11A-11C, or plural indicators 49 as illustrated in FIG. 11D, or another indicator type. Human-readable indicia 140 is preferably provided on guide 136 so that each opening 138 on guide 136 has the same indicia 140 as indicia 47, 211 on holder 13" and exception storage apparatus 43. Indicia 140 further assists the technician to ensure that the correct medicament 11 is loaded into the correct guide 136 opening 138. Guide 136 indicators 49 are connected to PLC 79 through appropriate conductors (not shown) permitting selective energizing and operation of indicators 49 to indicate the opening 138 through which each medicament 11 is to be loaded. Guide 136 may be made of any suitable material such as metal, plastic, laminate or a combination of materials.

Docking station 15" is otherwise identical to docking station 15 previously described and illustrated and the description of docking station 15 is incorporated by reference. Controller 17, as previously described, controls operation of docking station 15" and indicators 49 on guide 136 and holder 13", docking station 15", and controller 17 may be used as part of an item-management system, such as system 10 or 10' (FIGS. 12A, 12B).

FIGS. 14-17 are exemplary screen displays of a type which could be displayed to a technician or pharmacist on display 125 for purposes of implementing system 10 or 10' using holder 13, 13', or 13" and docking station 15, 15', or 15". The screen displays of FIGS. 14-17 are intended to represent non-limiting examples as the type and number of screen displays can be modified and the information provided in the screen displays may be customized to meet the needs of the particular pharmacy, hospital, long-term care facility or other operator. For convenience and brevity, the screen displays of FIGS. 14-17 are described in connection with system 10 including holder 13 and docking station 15, it being understood that the screen displays and methods of implementing system 10 are applicable for use with system 10' or with holder 13', 13" and docking station 15', 15".

Referring to the screen displays of FIGS. 14-17, a technician or registered pharmacist initiates use of system 10 by logging on to the system 10, preferably at docking station 15. Preferably, loading of holder 13 is performed by a technician while verification of the loaded holder 13 is performed by a registered pharmacist.

Figure 14:
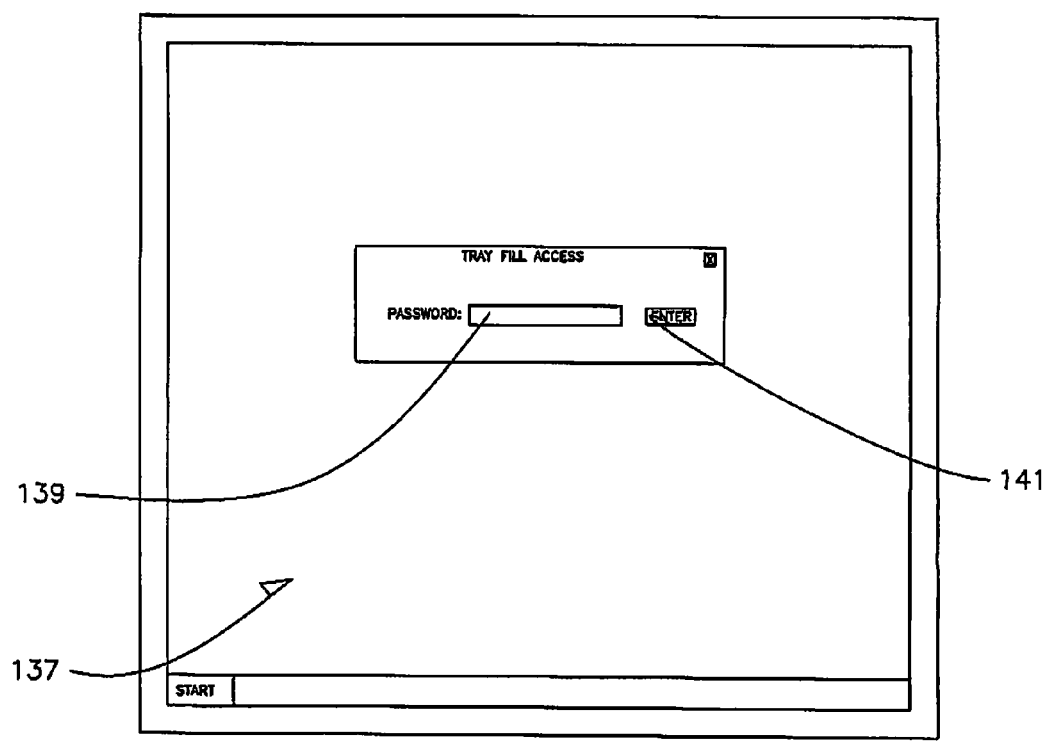
FIG. 14 is an exemplary log-on screen display.

Referring to FIG. 14, the technician is initially presented with a log-on screen 137 displayed on video display 125. The technician logs on to the system 10 by keying his or her password into the password field 139 using keyboard 127 and selecting the ENTER icon 141. Alternatively, the technician could utilize biometric device 130 to identify herself to the system 10. The technician's password information is transmitted to server 107 (or server 124 in system 10'), whereupon it is determined that the technician is an authorized user.

Figure 2:
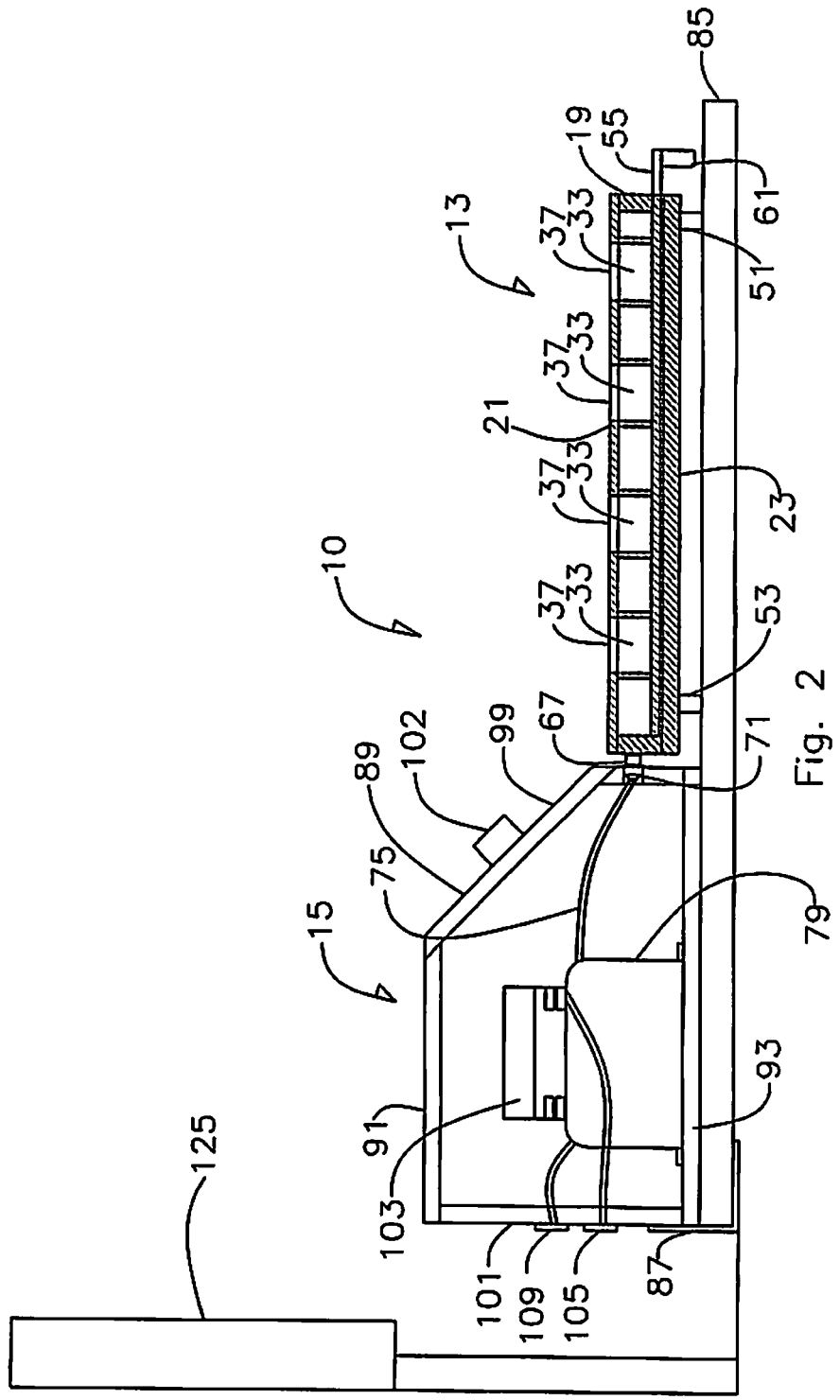
FIG. 2 is a schematic side sectional view of the representative holder and docking station taken along section 2-2 of FIG. 1.

If a holder 13 is not already docked at docking station 15 as shown in FIGS. 1-3 (or is not in wireless communication with docking station 15' as in FIG. 6), a further screen (not shown) may be displayed on video display 125 prompting the technician to dock a holder 13 at docking station 15. In the example of FIGS. 1-3, holder 13 is shown docked at docking station 15 by insertion of pin 65 in receiver 63, thereby positioning holder 13 to form an electrical connection between holder contacts 67, 69 and docking station contacts 71, 73. Identification element detector 83 identifies the unique identifier element embedded in holder 13. Detector 83 preferably detects an RFID-type identification element 81 to identify holder 13 to system. If the docked holder 13 is recognized by system 10 (or if wireless-type holder 13' is recognized by system 10), indicator lamp 102 is activated to inform the technician that the system 10 is in a ready state. Proximity detector 66 may also indicate to controller 17 that holder 13 is properly docked at docking station 15.

Figure 15:
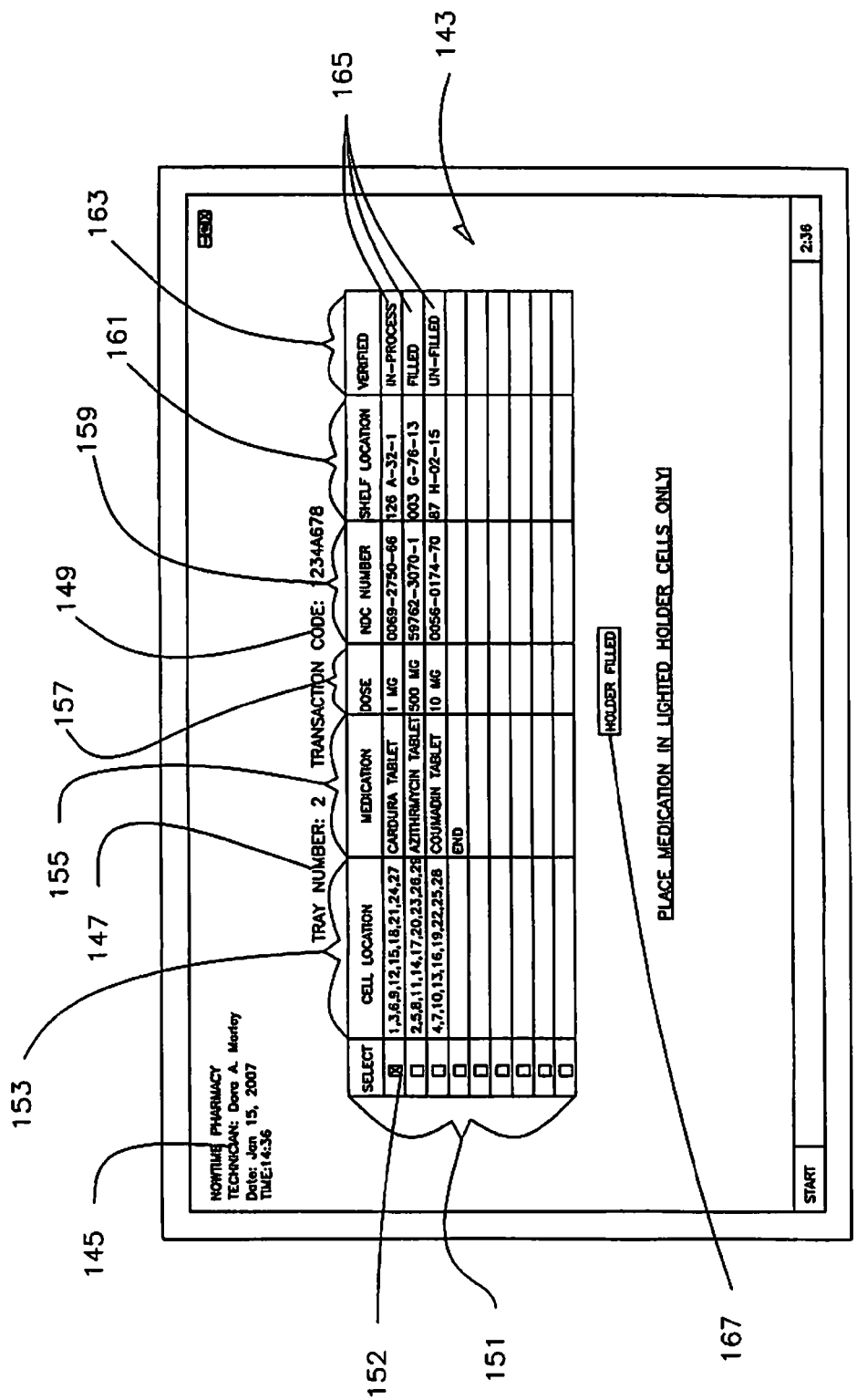
FIG. 15 is an exemplary screen display for loading of a holder.

Referring next to FIG. 15, if the technician is authorized and if holder 13 is docked and recognized, then a holder-loading screen 143 is displayed on video display 125. Holder-loading screen 143 provides information for loading each medicament 11 into the correct cell 33.

Information which may be presented on holder-loading screen 143 can include an identification field 145 identifying the operator name (e.g., Nowtime Pharmacy), technician name, and date and time-of-day on which holder 13 is being loaded. Additional information which may be displayed in connection with screen 143 is the holder identifier 147 and transaction code 149 which indicates the transaction corresponding to loading of the holder 13 for record-keeping purposes. Preferably, the transaction number and all other information relating to loading and verification of holder 13 is stored in a database on server 107 or 124. Holder identifier 147 may be any symbol or group of symbols capable of distinguishing one holder 13 from another holder 13. In the example, holder identifier 137 is identical to the identifier embedded in RFID tag-type identification element 81. In the example, the holder identifier 147 is the number 2. A unique identifier 147 can be important if more than one identical holder 13 is used by the pharmacy, hospital, long-term care provider or other operator.

Referring further to FIG. 15, holder-loading screen 143 includes information 151 required for loading of cells 33 of holder 13. Preferably, information 151 is displayed in the form of a graphical user interface (GUI), thereby facilitating ease of use by the technician. In the example, information 151 includes a select field 152, a cell location field 153, a medication type field 155, a dosage strength field 157, an NDC number 159 field, a shelf location 161 field, and a status 163 field. In the example, information 151 is displayed for each medicament 11 to be loaded into holder 13. In the example of FIG. 15, three medicament 11 types, namely, Cardura tablets, Azithrmycin tablets, and Coumadin tablets are to be loaded into holder 13.

The cell location field 153 identifies the cell 33 into which medicament 11 is to be loaded by referencing the human-readable indicia 47 associated with the designated cell 33. In the example, Cardura tablets are to be loaded into cells of holder 13 associated with the human-readable indicia 47 represented by numbers "1, 3, 6, 9, 12, 15, 18, 21, 24, 27" while the other medicaments are to be loaded into the other cells 33 of holder 13 identified in the cell location field 153. The ordering of the medicaments 11 is determined by the order in which the medicaments 11 are required in order to load each container or containers (e.g., a vial, bottle, blister package, or pouch package) for each prescription order or dispense request. For example, server 107 may order the medicaments 11 presented on screen 143 based on the sequence in which prescription orders or dispense requests are to be filled for more than one patient or may order the medicaments 11 presented on screen 143 based on a drug regimen for a single patient, for example, ordering the medicaments by the time of day the medicaments 11 are to be taken by the patient (e.g., breakfast, lunch, and dinner). The slow mover medicaments 11 indicated on screen 143 may be arranged and ordered for serial dispensing (i.e., one-after-the-other) or may be arranged and ordered to alternate with medicaments dispensed from other storage apparatus (e.g., cassettes, cells, canisters, etc.) within automated dispensing machine 45.

The medication type field 155 and dosage strength field 157 information refers to the type and strength of the medicament 11, while the NDC number field 159 information refers to the 10-digit National Drug Code (NDC) number for the specific medicament 11 called for by the prescription order or dispense request.

The shelf location field 161 information refers to the shelf location of the pharmacy, hospital, long-term care facility, or the like at which the medicament container, for example representative container 135 (FIG. 1), holding a medicament 11 is located. This information is provided to assist the technician in retrieving the container 135 from storage. In the example, fictitious alpha-numeric shelf locations are displayed.

Figure 7:
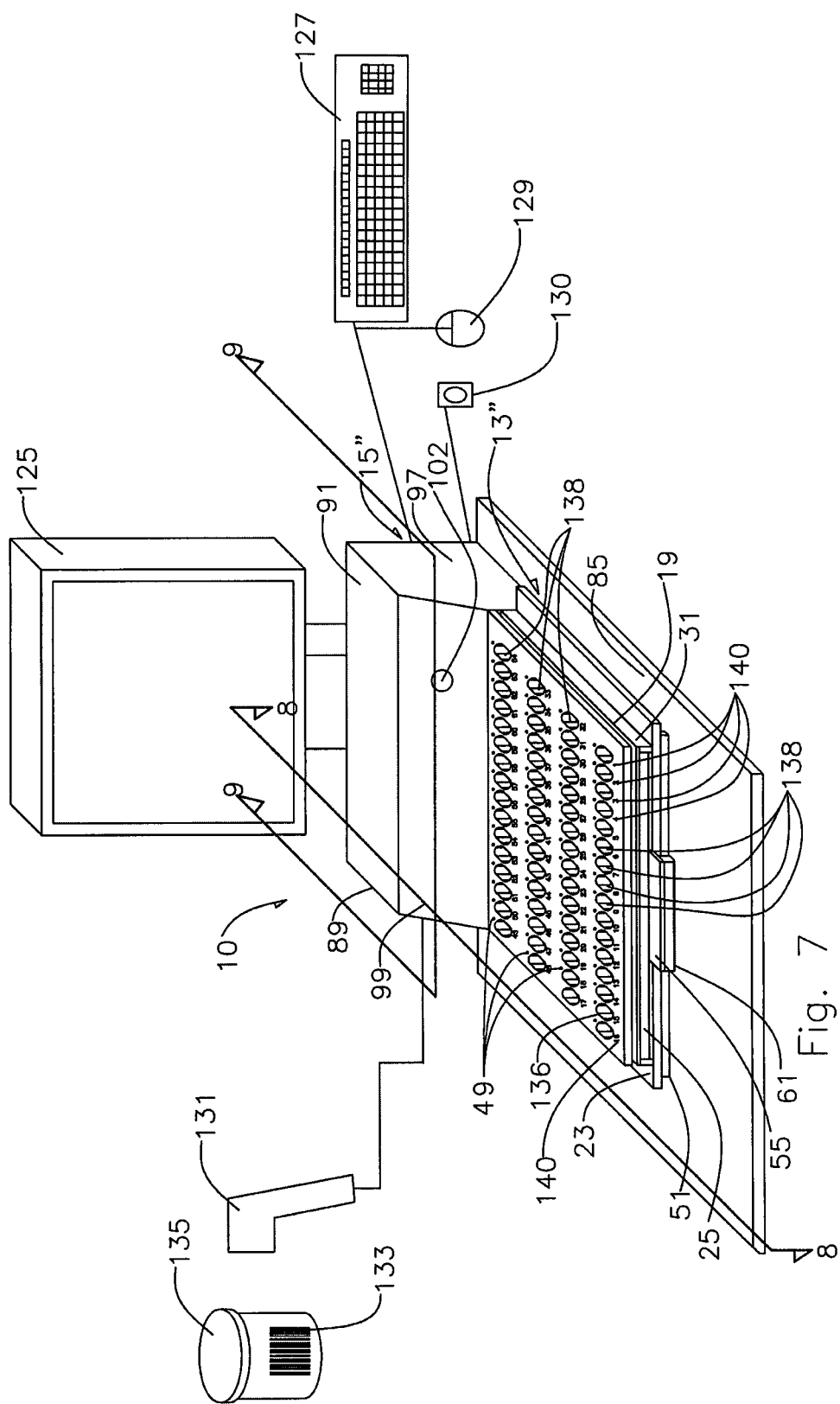
FIG. 7 is a perspective view of a further exemplary embodiment showing a docking station with a guide, and a holder docked at a docking station.
Figure 8:
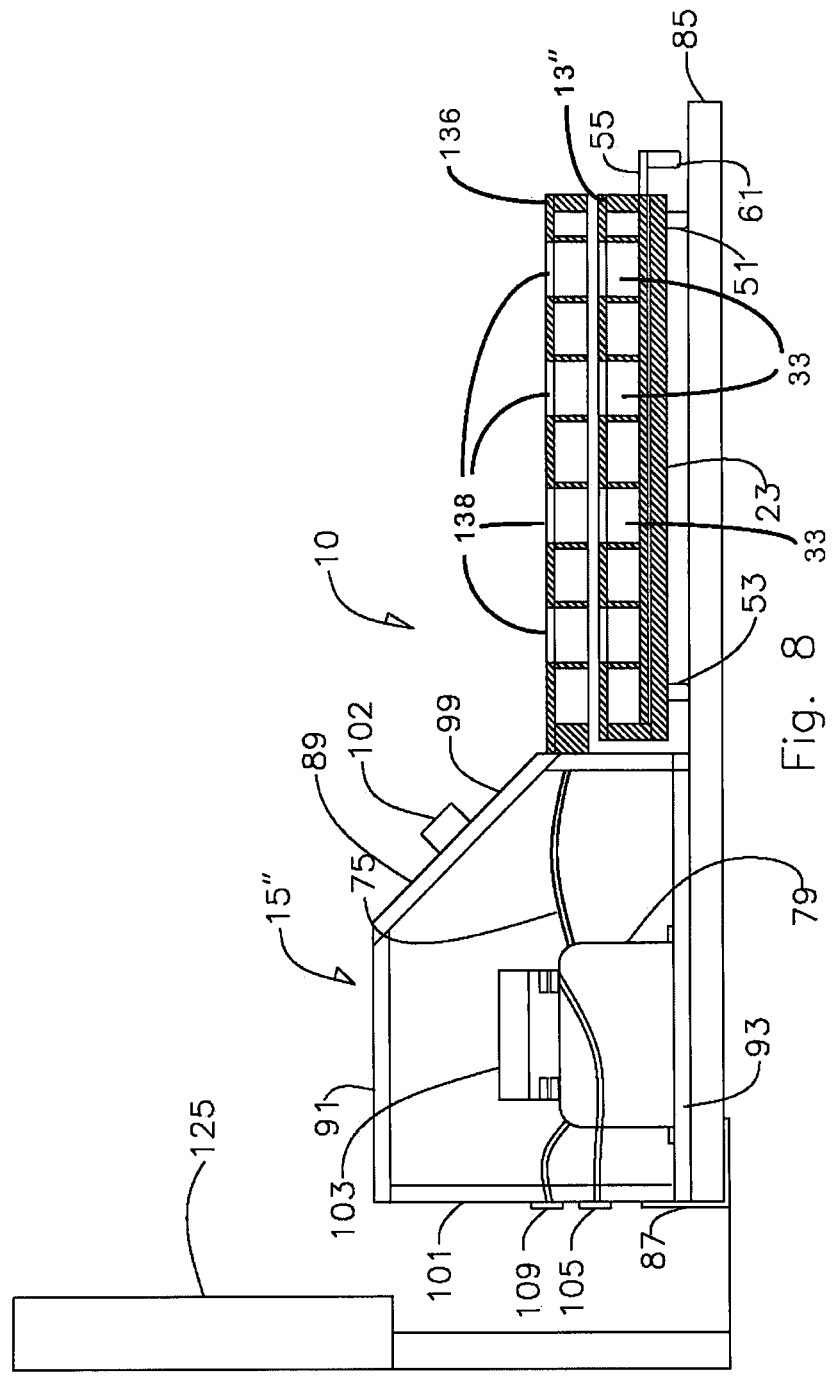
FIG. 8 is a schematic side sectional view of the further exemplary docking station and guide taken along section 8-8 of FIG. 7.
Figure 9:
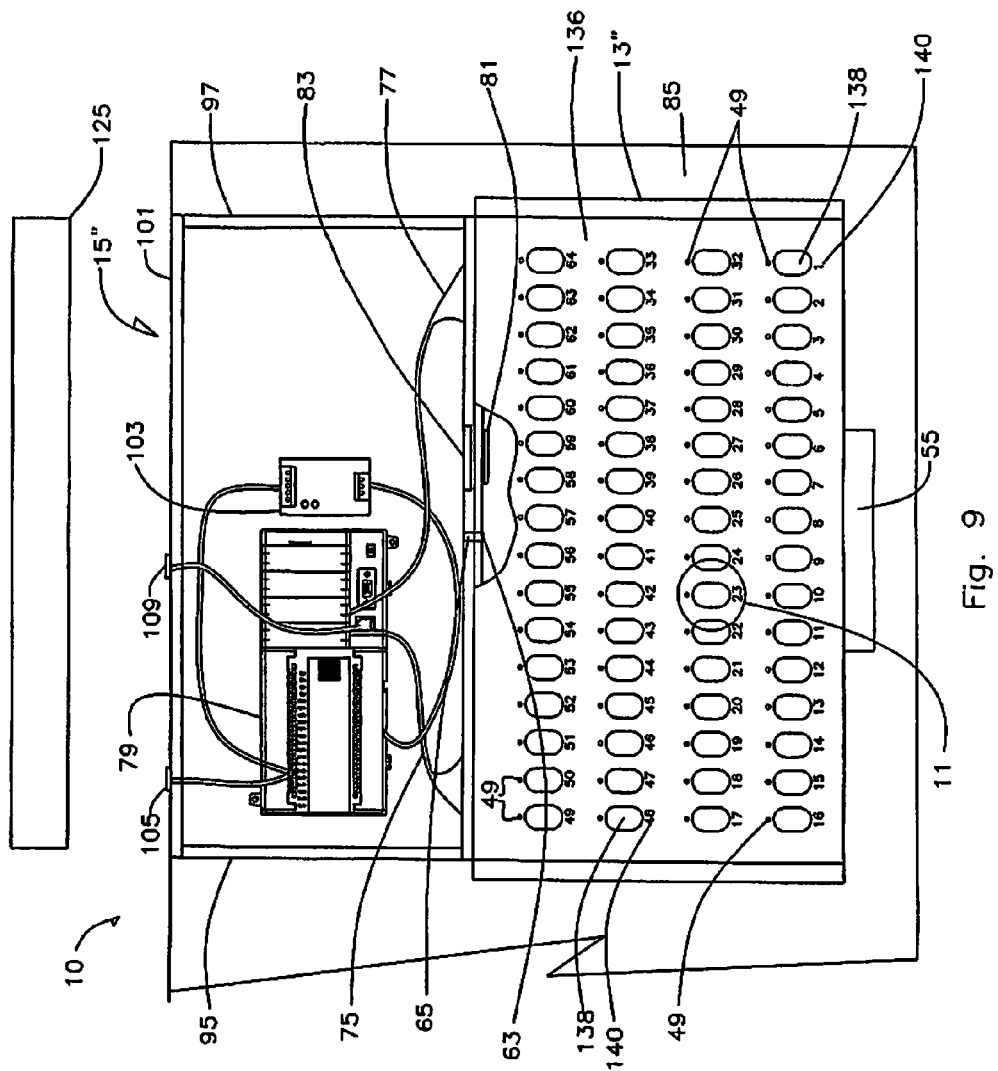
FIG. 9 is a schematic top sectional view of the further exemplary docking station and guide taken along section 9-9 of FIG. 7.
Figure 10:
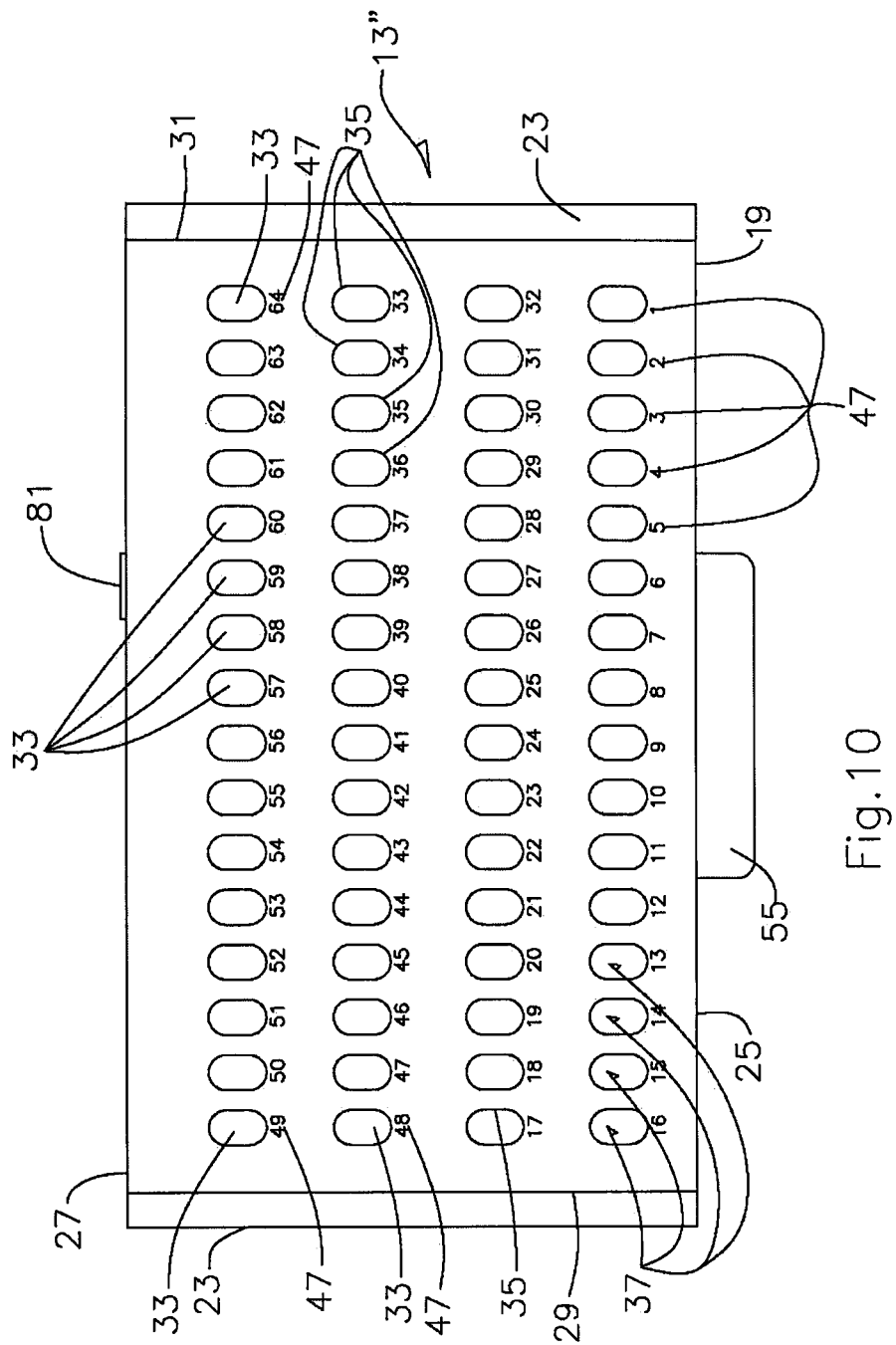
FIG. 10 is a top side view of the holder shown in FIGS. 7-9 shown apart from the docking station.

As illustrated in FIGS. 1 and 7, it is envisioned that the technician will scan the bar code 133 on the container 135 with bar code scanner 131. Program of instructions 115 running on server 107 can then verify that the correct container 135 has been selected from storage based on information contained in bar code 133. The technician can also verify that the correct medicament container 135 has been selected by comparing the medication type 155, strength 157, and human-readable NDC information 159 on the screen 143 with human-readable information on the label for container 135.

The status information field 163 indicates the status of the holder-loading process. Selection of each medicament 11 for loading can be made simply by touching the technician's finger on the row 165 of touch-screen video display 125 associated with one medicament 11 or by selecting the row 165 with another input device, such as keyboard 127 and mouse 129. In the example of FIG. 15, the technician is in the process of loading Cardura tablets into cells 33. This is indicated by the row 165 associated with Cardura tablets having been selected as indicated by the X character in the select field 152 and the IN-PROCESS text in status information field 163. The row 165 associated with the Azithrmycin tablets indicates FILLED in the status information field 163 indicating that loading of the Azithrmycin tablets has been previously completed. The row 165 associated with the Coumadin tablets has not yet been selected as indicated by the UNFILLED indication in field 153.

PLC 79 (or computer 117 in system 10') selectively activates the indicator 49 for each cell 33 into which the medicament 11 is to be loaded once the appropriate row 165 associated with the medicament is selected. This pick-to-light feature enables the technician to load medicaments 11 without any necessity for reliance on written loading instructions. Thus, in the example of FIG. 15, the indicator 49, preferably an LED lamp, associated with each of cells 33 indicated by the human-readable indicia 47 "1, 3, 6, 9, 12, 15, 18, 21, 24, 27" is energized to tell the technician to load a Cardura tablet into each of these cells 33. Each indicator 49 associated with each other cell 33 of holder 13 is not activated. Activation of only each indicator 49 associated with the cell to be loaded is referred to herein as selective indicator 49 activation or operation.

Once all cells 33 associated with a row 165 are filled, the technician then selects the next row 165 of medicaments to be filled and proceeds to load holder 13 as directed by indicators 49. Selection can again be accomplished by touching the technician's finger on the row 165 of touch-screen video display 125 associated with the next medicament 11 to be loaded in holder 13 or by selecting the row 165 with the keyboard 127 or mouse 129. The indicator or indicators 49 previously activated are deactivated and the appropriate indicators 49 for the next medicament 11 to be loaded are activated. This process is repeated until all medicaments 11 have been loaded in holder 13 as called for by screen 143.

Once all cells 33 of holder 13 are loaded as required by holder-loading screen 143, the technician clicks on, or otherwise selects, the HOLDER FILLED icon 167. Selection of icon 167 sends a signal to server 107 (or server 124 in system 10' indicating that loading of holder 13 has been completed. Each loaded holder 13 can subsequently be verified by a registered pharmacist prior to loading of medicaments 11 from loaded holder 13 into automated dispensing machine 45.

Referring now to FIG. 13, a storage cabinet 169 may optionally be provided to store one or more holder 13, 13a, 13b, and 13c thereby facilitating loading and verification of multiple holders. In the example, each holder represented by reference numbers 13a, 13b and 13c has structure identical to holder 13. Loaded holders 13, 13a, 13b, and 13c may be stored in cabinet 169 after loading and before verification or may be stored in cabinet 169 after verification by a registered pharmacist and before loading of the verified medicaments 11 into exception storage apparatus 43 of automated dispensing machine 45.

If provided, storage cabinet 169 includes top and bottom walls 171, 173, sidewalls 175, 177, and a front opening 179 through which holders (e.g., holder 13) are placed into cabinet 169. Stacked opposed slot pairs 181,183 may be provided to receive the bottom 23 of each holder 13 permitting holders 13, 13a, 13b, and 13c to be stored in cabinet 169.

Figure 16:
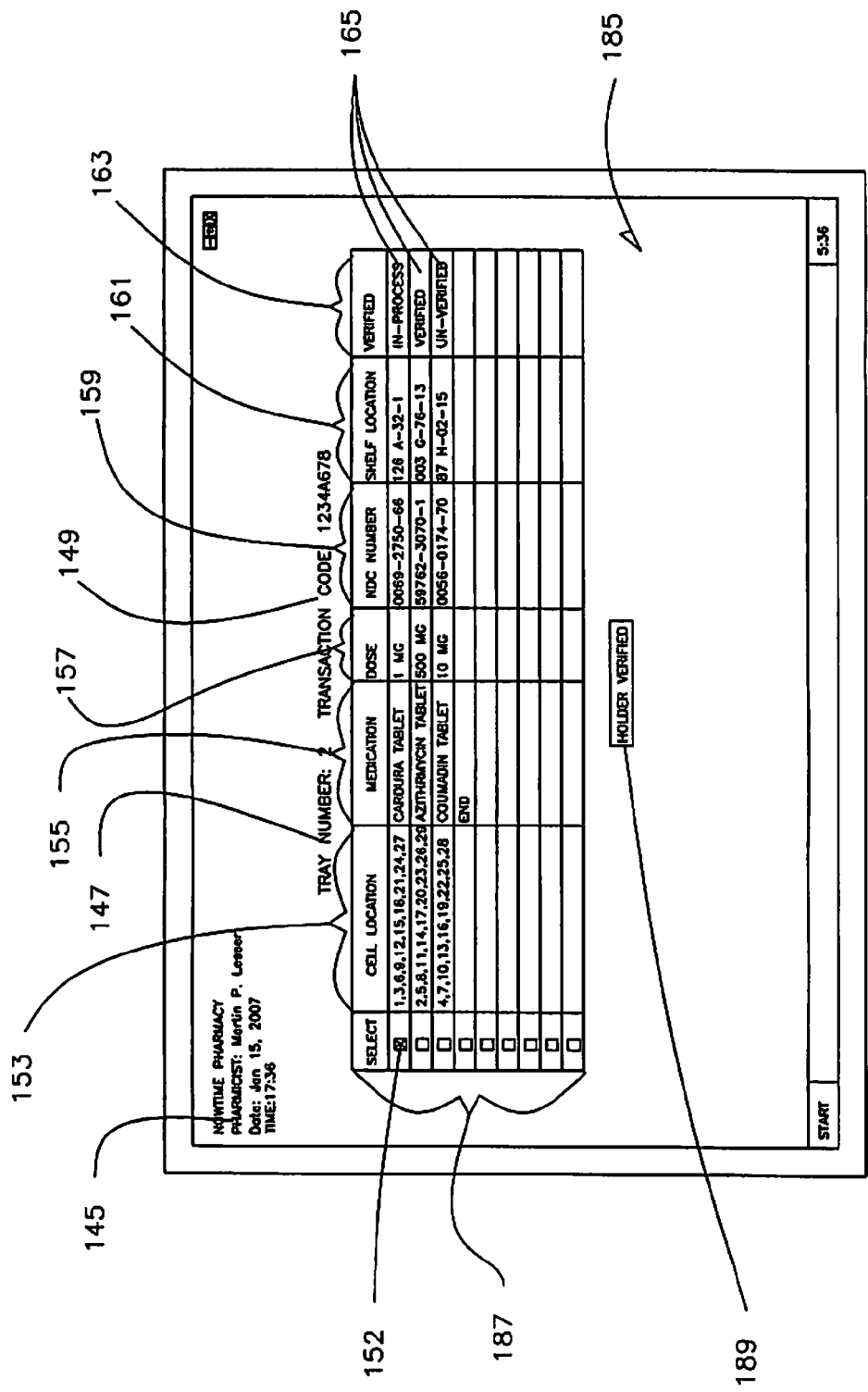
FIG. 16 is an exemplary screen display for verification of the items loaded in the holder.

As already noted, each loaded holder 13 can be verified by a registered pharmacist to ensure that each cell 33 has been loaded with the correct medicament 11. FIG. 16 shows an exemplary holder-verification screen 185 which corresponds to the holder-loading screen 143 for that holder 13. Holder-verification screen 185 includes information 187 required for verification of the medicaments 11 loaded into cells 33 of holder 13. This information is essentially identical to that displayed in connection with holder-loading screen 143. For convenience and simplicity, reference numbers of information displayed on holder-loading screen 143 are used again to identify corresponding fields of information on holder-verification screen 185.

As with the holder-loading screen 143, an identification field 145 can be provided to identify the operator name (e.g., Nowtime pharmacy), name of the pharmacist responsible for medicament 11 verification, and the date and time-of-day on which holder 13 is verified. The holder identifier 147 and transaction code 149 are also preferably displayed for the same purpose as described in connection with the holder-loading screen 143.

Preferably, information 187 is again displayed in the form of a graphical user interface (GUI), thereby facilitating ease of use by the verifying pharmacist. In the example, the displayed information 187 again includes a select field 152, a cell location field 153, a medication type field 155, a dosage strength field 157, an NDC number field 159, a shelf location field 161, and a status information field 163 including the information described in connection with holder-loading screen 143. In the example, information 187 is again displayed for each medicament 11 to be loaded into holder 13. In the example of FIG. 16, the Cardura tablets, Azithrmycin tablets, and Coumadin tablets previously loaded into cells 33 of holder 13 are presented for verification by the pharmacist.

In order to verify that each cell 33 holds the correct medicament 11, the pharmacist simply selects the row 165 to be verified. Selection is accomplished by touching the touch screen display 125 on row 165 or by selecting row 165 with the keyboard 127 or mouse 129. The status information field 163 again indicates the status of the holder-verification process.

Referring further to FIG. 16, the screen display 185 shows an example of displayed information for verification that the Cardura tablets have been correctly loaded into the cells 33 indicated by the human-readable indicia 47 "1, 3, 6, 9, 12, 15, 18, 21, 24, 27" located on holder 13. Selection of the Cardura tablets for verification is indicated in the example by the row 165 associated with Cardura tablets having been selected as indicated by the X character in the select field 152 and the IN-PROCESS text in status information field 163. The row 165 associated with the Azithrmycin tablets indicates VERIFIED in the status information field 163 indicating that verification of the Azithrmycin tablets has been completed. The row 165 associated with the Coumadin tablets has not yet been selected for verification as indicated by the UN-VERIFIED indication in field 163. A selected row 165 can also be highlighted to facilitate identification of the row 165 then being verified.

Figure 17:
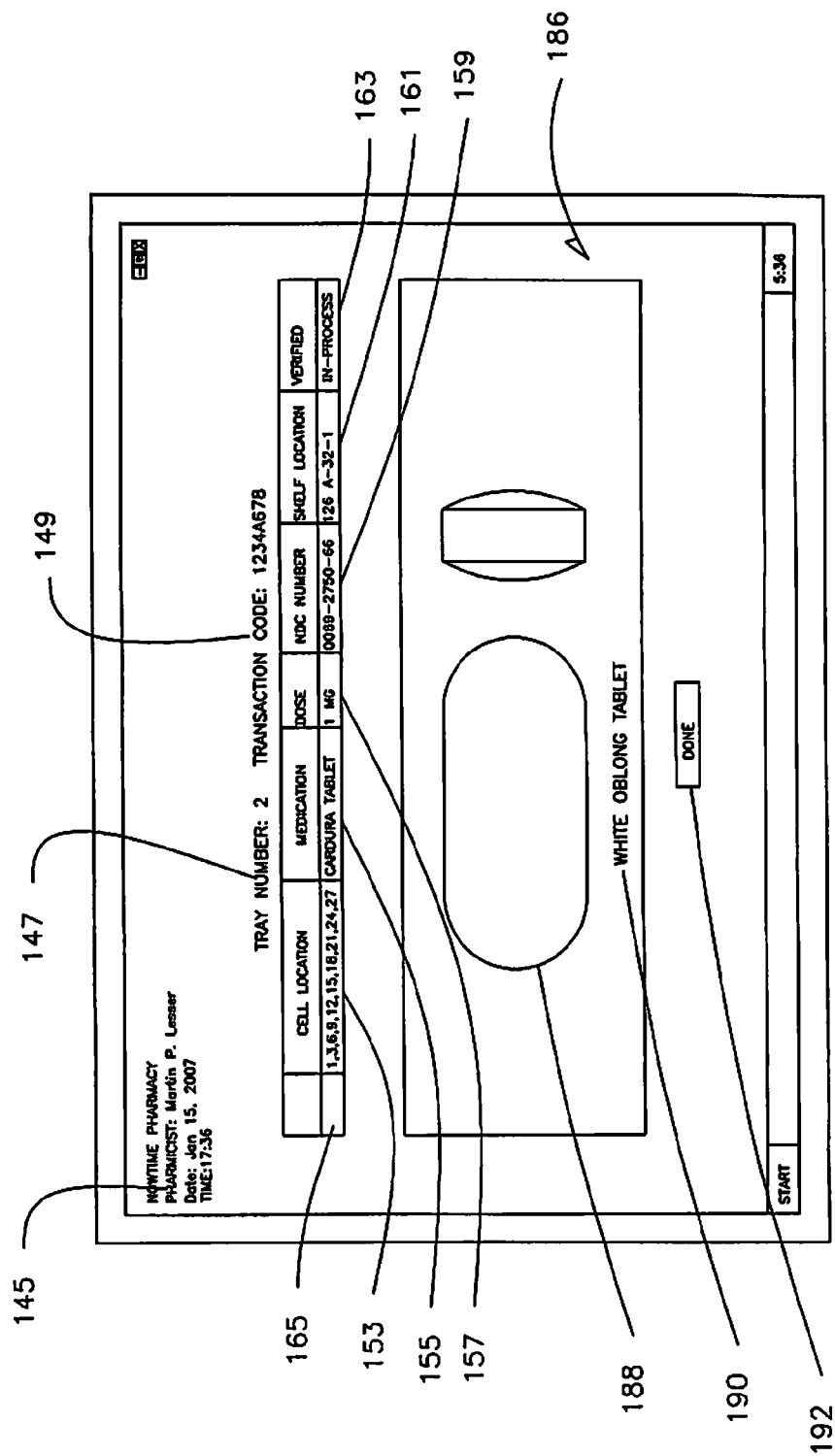
FIG. 17 is an exemplary screen display for verification of the items loaded in the holder including a reference image of a medicament.

Referring next to FIG. 17, a further verification screen display 186 may be provided to assist the pharmacist with the verification process. As each row 165 is selected, a medicament-specific verification screen 186 may be displayed. In the example, screen 186 displays the row 165 being verified including the cell location field 153, medication type field 155, dosage strength field 157, NDC number field 159, shelf location field 161, and status information field 163. Screen 186 also displays a reference image of the physical appearance of the medicament 188 together with a word description 190 of the physical appearance of the medicament 11. In this example of the Cardura medicaments 11, the word description 190 is white oblong tablet. A screen display similar to display 186 of FIG. 17, including a reference image 188 and word description 190, may be displayed to the technician during the holder-loading process associated with screen 143 to assist the technician in placing the correct medicament(s) 11 into each cell 33.

Upon selection of a row 165, PLC 79 of controller 17 again selectively activates each indicator 49, preferably an LED lamp, for each cell 33 to be verified by the pharmacist. As with the loading process, this pick-to-light capability enables the pharmacist to rapidly confirm that the correct medicament 11 has been loaded into the correct cell 33 without the necessity for reliance on written verification instructions. The pharmacist can quickly compare the physical appearance of each medicament 11 in each indicated cell 33 without the necessity of reliance solely on written instructions. This process is facilitated by presentation of screen 186 and the reference image and description information 188, 190 as the pharmacist can quickly compare the appearance of the medicament 11 on screen 186 with the appearance of the medicament(s) 11 in each cell 33 associated with an activated indicator 49.

Thus, in the verification example of FIGS. 16-17, each indicator 49 associated with each of cells indicated by the human-readable indicia 47 "1, 3, 6, 9, 12, 15, 18, 21, 24, 27" into which Cardura tablets was to be loaded, is activated by PLC 79 of controller 17 (or computer 117 in system 10') during the verification process. Each other indicator 49 is inactive.

If screen 186 is provided, selection of the DONE icon 192 returns the pharmacist to screen 185 for selection of the next medicament 11 to be verified. Once all cells 33 associated with a row 165 are verified, the technician then selects the next row 165 of medicaments to be verified and proceeds to verify the medicament(s) in each cell 33 as directed by indicators 49. The indicator or indicators 49 previously activated are deactivated and the appropriate indicators 49 for the next medicament 11 are activated. This process is repeated until all medicaments 11 have been verified as called for by screen 185.

Once all rows 165 and medicaments 11 are verified, the pharmacist selects the HOLDER VERIFIED icon 189. Selection of icon 189 sends a signal to server 107 of system 10 (or server 124 of system 10') indicating to system 10 that holder 13 has been fully verified and that the medicament 11 contents are in the correct cells 33 ready for use with automated dispensing machine 45. A record may be made of the verified medicament 11 contents of holder 13 cells 33 which may be stored in a database residing on server 107 (or server 124). Such a record is useful in further confirming that the correct medicaments 11 were loaded in holder 13. Each verified holder 13 can then be stored in cabinet 169 awaiting use, or the holder 13 and its medicament 11 contents can be taken directly to automated dispensing machine 45 for immediate loading of medicaments 11 into exception storage apparatus 43.

Figure 18:
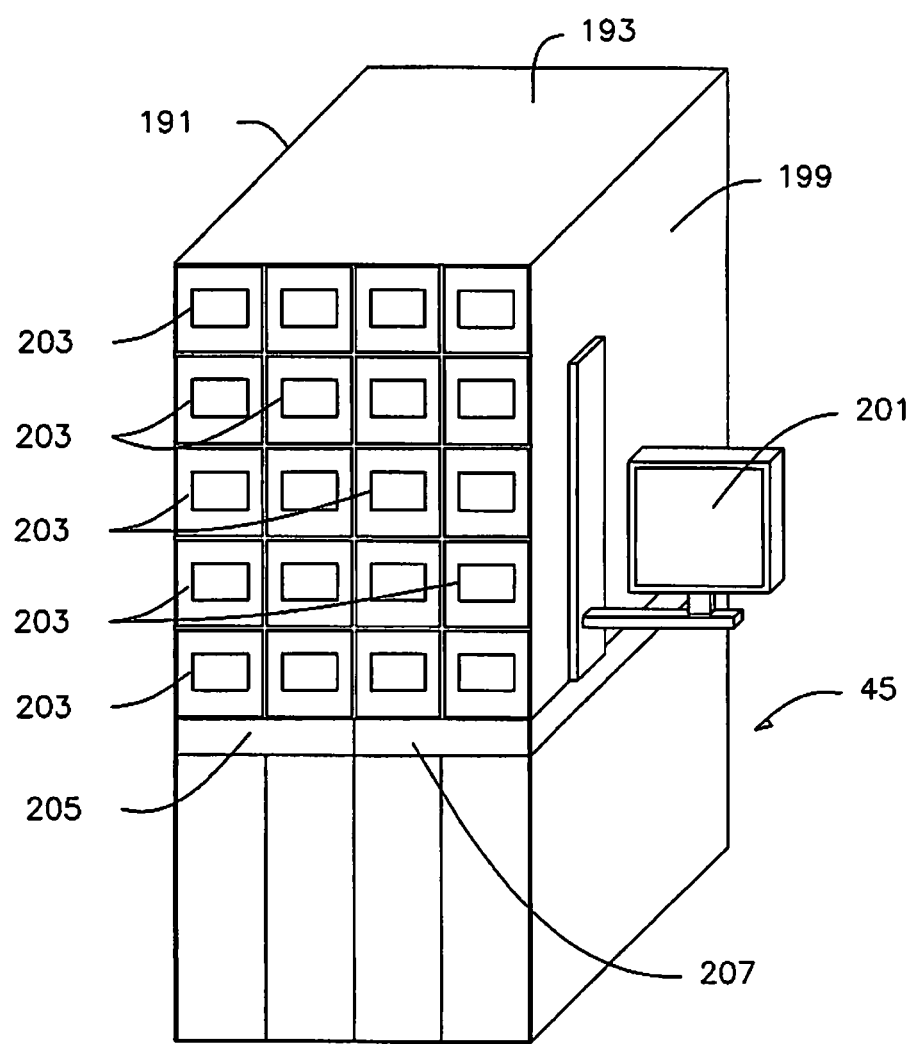
FIG. 18 is a perspective view of an exemplary automated medicament dispensing machine with which the representative holders of FIGS. 1-10 may be utilized.

Referring now to FIGS. 18-20, there is shown an exemplary automated dispensing machine 45 and exception storage apparatus 43 which may be quickly and accurately loaded with medicaments 11 using holder 13 or 13' or 13". Dispensing machine 45 includes a cabinet 191 with top and bottom walls 193, 195 and left and right sidewalls 197, 199. A touch-screen video display 201 is mounted to sidewall 199. Display 201 includes controls permitting a technician or pharmacist to control operation of dispensing machine 45 and to receive information about the status of the medicament filling process.

Exemplary dispensing machine 45 includes twenty pull-out drawers of which drawers 203 are exemplary. In the example, drawers 203 are organized into five rows of four drawers 203. Each drawer 203 supports a plurality of removable cassette-type storage apparatus (not shown), each of which stores a large quantity of bulk-form medicaments 11. The cassettes can be replenished as medicaments 11 stored therein are depleted.

Exemplary dispenser 45 further includes a pair of doors 205, 207 which cover exception storage apparatus 43 as shown in FIG. 18 and which can be opened as shown in FIGS. 19-20. As previously described, exception storage apparatus 43 may be provided to store and to dispense "slow mover" medicaments 11 loaded therein. In the example, dispenser 45 includes a single exception storage apparatus 43. However, any number of exception storage apparatus 43 may be provided based on the needs of the operator.

In the example, exception storage apparatus 43 is a drawer or tray-like device which can be pulled out from cabinet 191 as shown in FIGS. 19-20. When in the state of FIGS. 19-20, automated dispensing machine 45 is temporarily shut down and is out of service and unavailable to fill prescription orders and dispense requests while exception storage apparatus 43 is pulled out from cabinet 191. Therefore, it is important to load exception storage apparatus 43 as promptly as possible to return dispensing machine 45 to service.

Figure 22:
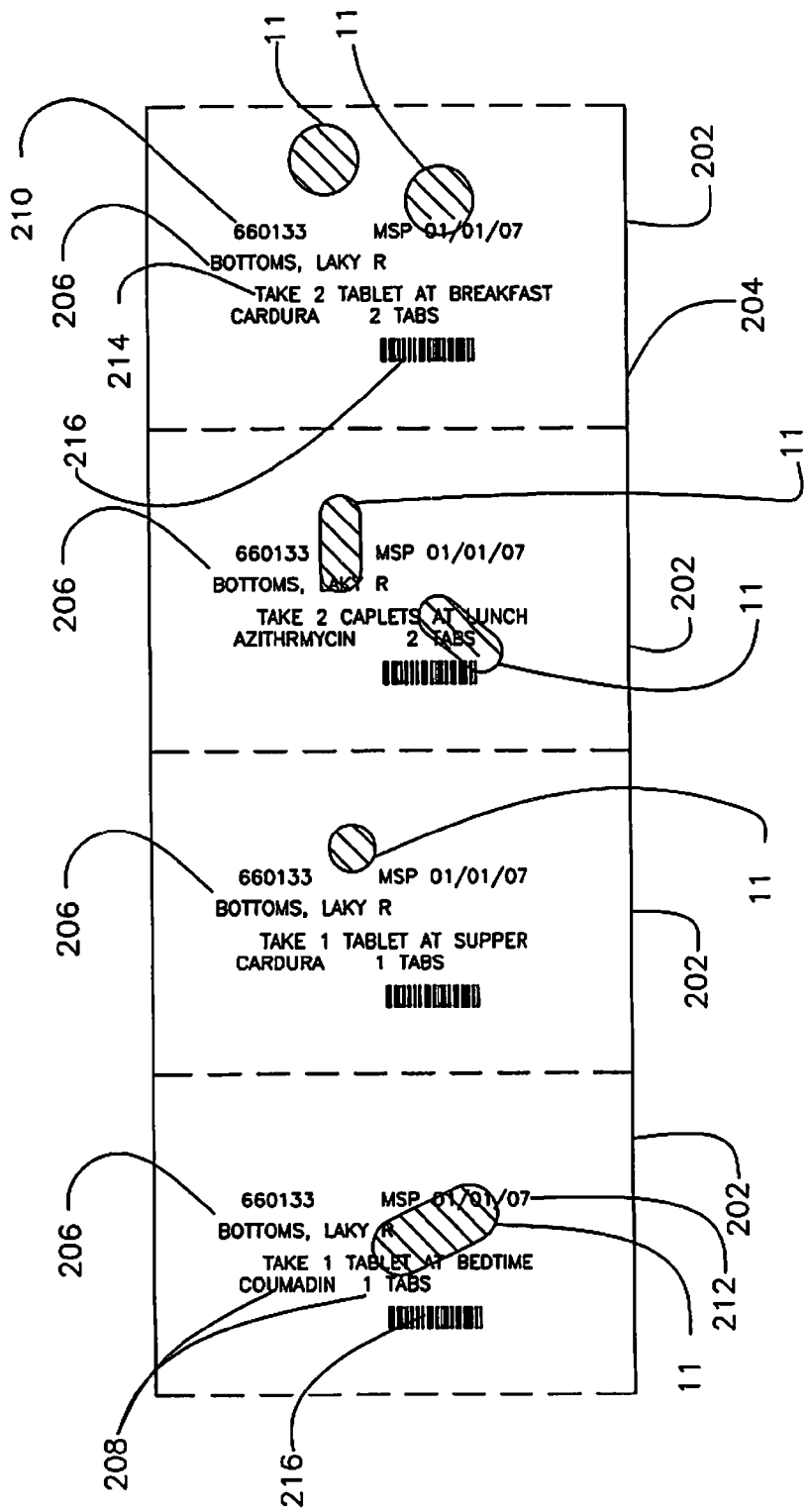
FIG. 22 is an exemplary series of medicament-containing pouch packages of the type produced by the automated dispensing machine of FIGS. 18-20.

The exception storage apparatus 43 shown in FIGS. 19-20 can be described as having a somewhat flat and narrow configuration with a plurality of cells 41 provided therein. Each cell 41 of exception storage apparatus 43 is capable of storing one medicament 11, or a small quantity of medicaments 11 as illustrated in FIGS. 21A-22. In the example, cells 41 include 64 total cells grouped in four rows of 16 cells.

Cells 41 are indexed for movement along a track (not shown) in exception storage apparatus 43. Cells 41 are indexed forward along the track toward an opening (not shown) in the bottom of apparatus 43 so that the contents of each cell 41 fall through a cell bottom opening (not shown) and to a packaging device within dispensing machine 45 through chutes, hoppers or other guide structure, or by a mechanical device such as an auger. Medicaments 11 may be discharged from cells 41 by any other suitable means including a movable gate (not shown) over a cell bottom outlet (not shown), or by a solenoid, air-powered actuator, air-jet, or mechanical arm which ejects the medicament through an upper cell inlet 209 of the type shown in FIG. 19A. The medicaments 11 fall via chutes, guides to a packaging device or are directed to packaging device by mechanical means (e.g. an auger).

In the example, automated dispensing machine 45 includes a pouch-package-type packaging apparatus (not shown) within a lower portion of cabinet 191. Alternatively, packaging apparatus capable of packaging medicaments 11 into other container types (e.g., bottles, vial, blister packages) may be utilized. A pouch-package-type packaging device includes a form-fill-seal packaging device. A "form-fill-seal" packaging device forms a package (i.e., a pouch) in a web of packaging material, fills the package with the medicament(s), and seals the package forming a plurality of discrete packages, or pouches.

In the example, one or more medicament 11 discharged from the cassette-type storage apparatus (not shown) or exception storage apparatus 43 is loaded into separate pouches 202 formed (e.g., by heat-sealing or sonic welding) in a web of packaging material 204 as illustrated in FIG. 22. Information can be printed on each pouch 202 by a printer (not shown) associated with dispenser 45 and such information can include the patient's name 206, medicament name and quantity 208, prescription number 210, date 212, instructions for taking the medicament 214 (such as time of day the medicament is to be taken) and machine-readable indicia 216 (such as a bar code) representative of the aforesaid information. Pouch packages are ideal for use in administering medication regimens because the exact medicaments to be taken at a given time can be packaged together in a single pouch, and the pouches can be organized and labeled in the exact order in which each medicament is to be taken, for example, morning, noon and evening. An exemplary automated dispensing machine 45 is a model ATP 320, 371, or 384 dispensing machine available from The Chudy Group, LLC of Powers Lake, Wis.

Transfer of medicaments 11 from holder cells 33 to exception storage apparatus 43 will now be described in connection with FIGS. 21A-21C. In the example, cells 33 of holder 13 are positioned and arranged so that they have a pattern which is identical to that of cells 41 in exception storage apparatus 43. Holder 13, therefore, can be placed directly on top of exception storage apparatus 43 as shown in FIG. 20 and FIGS. 21A-21C with each cell 33 and 41 completely aligned and in registry. In the example, holder 13 and exception storage apparatus 43 each have 64 total cells 33, 41 grouped in four rows of 16 cells. Human-readable indicia 211 is preferably provided on exception storage apparatus 43 (FIG. 19A) so that each cell 33 on holder 13 has the same indicia 47 as indicia 211 on exception storage apparatus 43. The cell 33 pattern and indicia 47 of holder 13 is most preferably identical to the cell 41 pattern and indicia 211 of exception storage apparatus 43.

Referring again to FIGS. 20 and 21A-21C, the verified holder 13 is taken to exception storage apparatus 43 of dispensing machine 45 by a technician or pharmacist. Holder 13 is set on top of exception storage apparatus 43. Legs 51, 53 position holder 13 over exception storage apparatus 13 as shown, for example, in FIGS. 21A-21C to ensure that holder 13 is in the correct orientation on exception storage apparatus 43 with correct alignment of cells 33, 41. Once aligned, holder 13 is initially in the position shown in FIG. 21A.

At this point in the process, identification element 81 is detected by detector 84 of dispensing machine 45. If the correct holder 13 is positioned over exception storage apparatus 43, the technician/pharmacist is given a prompt signal by video display 201. If an incorrect holder 13 is positioned over exception storage apparatus 43, then display 201 prompts the technician/pharmacist to not transfer the medicaments 11 and may present an error message and/or alarm. In addition, system 10 or 10' may deactivate dispenser 45 preventing dispenser 45 operation until the correct holder 13 is in place or the technician/pharmacist overrides the system 10, 10'.

Prior to medicament 11 transfer and as shown in FIG. 21A, shuttle member 55 is in its "closed" position with cell 33 outlets 39 covered by shuttle member 55. Medicaments 11 cannot exit cells 33 in this closed position.

Next, and as shown in FIG. 21B, the technician grasps pull 61 and moves shuttle member 55 in the direction of arrow 217. Movement of shuttle member 55 in the direction of arrow 217 partially opens cell outlets 39 as openings 59 in shuttle member 55 are aligned with cell outlets 39. As a result, medicaments 11 begin to fall by means of gravity into the aligned cells 41 of exception storage apparatus 43.

Finally, and as shown in FIG. 21C, the technician moves shuttle member 55 fully in the direction of arrow 217 by means of pull 61 to fully align openings 59 in shuttle member 55 with cell outlets 39. Cells 33 are fully open in this position causing medicaments 11 in cells 33 to fall into the corresponding cells 41 of exception storage apparatus 43. Exception storage apparatus is now correctly loaded and is ready for dispensing and packaging of the slow mover medicaments 11 stored in cells 41. This loading process shown in FIGS. 21A-21C is very rapid (less than one minute) and enables automated dispensing machine 45 to be quickly returned to service.

Systems 10, 10' accurately and rapidly enable loading of medicaments 11 in the exact order in which the medicaments 11 are to be loaded into exception storage apparatus 43. The medicaments 11 are rapidly verified by the system 10, 10' and docking station 15 in a way which is not possible based solely in reliance on written instructions. This is because selective operation of the indicators 49 permits pharmacy personnel to load and verify the contents of holder 13 without having to take his or her eyes off of the holder 13 to read instructions. Each exemplary system 10, 10' therefore, speeds the holder-loading process while at the same time providing a high confidence level that each cell 33 and 41 has been loaded with the correct medicament 11. Accurate loading of medicaments 11, in turn, provides a better level of care for all patients which, of course, is always the primary objective of any pharmacy, hospital, long-term care facility or other caregiver.

And, time required for selecting, verifying, and loading medicaments 11 into the automated dispensing machine is significantly decreased. This frees pharmacists to better serve their patients and enables the automated dispensing machine 45 to be immediately returned to service. The result once again is improved patient care and reduced cost of operation to the pharmacy, hospital, long-term care provider or other operator.

While the principles of this invention have been described in connection with specific embodiments, it should be understood clearly that these descriptions are made only by way of example and are not intended to limit the scope of the invention.

What is claimed is:

1. A medicament-management system which enables a pharmacy user to rapidly and accurately hand-load medicament holder cells with medicaments, the system comprising:
   a portable medicament holder for transferring medicaments to an automatic dispensing machine, the holder having plural cells arranged in a pattern corresponding to a pattern of cells of the automatic dispensing machine, each holder cell defining a cell upper opening through which medicament is hand-loaded and an openable lower opening through which medicament is transferred from the holder cell to a corresponding adjacent cell of the pattern of automatic dispensing machine cells;
   a docking station to which the holder is temporarily docked during the hand-loading, the docking station enabling control of visible information viewable proximate the holder cells indicating yes and no states of the holder cells;
   indicators which communicate the visible information to the user;
   at least one controller controlling the visible information such that yes state information is viewable proximate each holder cell into which medicament is to be hand-loaded, thereby assisting the user to rapidly and correctly perform repetitive hand-loading of holder cells with correct medicament, the at least one controller including a computer and being operable to store information indicating holder cells into which medicament is to be hand-loaded and to activate and to deactivate the visible information;
   an input device operative by a user to indicate to the at least one controller that medicament has been loaded in each holder cell indicated by the yes state information; and
   a video display operably connected to the at least one controller and the video display is operable to display information indicating each holder cell into which medicament is to be loaded.

2. The system of claim 1 wherein the visible information is viewable directly on the holder.
3. The system of claim 1 further including a plurality of the holders.
4. The system of claim 1 wherein the holder includes a closure which closes and opens the cell lower openings.
5. The system of claim 4 wherein the closure is a sliding gate.
6. The system of claim 1 wherein the holder includes legs.
7. The system of claim 2 wherein the holder includes light-transmissive material and the visible information is viewable through the light-transmissive material.
8. The system of claim 1 wherein the holder includes first alignment structure, the docking station includes second alignment structure, and the first and second alignment structures cooperate to align the holder at the docking station.
9. The system of claim 1 wherein the docking station includes circuitry enabling the control.
10. The system of claim 1 wherein each indicator radiates light.
11. The system of claim 10 wherein each indicator includes an energizable light source.
12. The system of claim 11 wherein each indicator is on the holder.
13. The system of claim 1 wherein the at least one controller is operable to provide verification of a hand-loaded holder.
14. A medicament-management system which enables a pharmacy user to rapidly and accurately hand-load medicament holder cells with medicaments, the system comprising:
   a portable medicament holder for transferring medicaments to an automatic dispensing machine, the holder having plural cells arranged in a pattern corresponding to a pattern of cells of the automatic dispensing machine, each holder cell defining a cell upper opening through which medicament is hand-loaded and an openable lower opening through which medicament is transferred from the holder cell to a corresponding adjacent cell of the pattern of automatic dispensing machine cells;
   indicators which communicate visible information to the user, the visible information being viewable proximate at least one holder cell into which medicament is to be hand loaded;
   a docking station to which the holder is temporarily docked during the hand-loading, the docking station enabling control of the indicators; and
   at least one controller controlling the indicators, thereby assisting the user to rapidly and correctly perform repetitive hand-loading of holder cells with correct medicament, the at least one controller including a computer and being operable to store information indicating holder cells into which medicament is to be hand-loaded and to activate and to deactivate the visible information;
   an input device operative by a user to indicate to the at least one controller that medicament has been loaded in each holder cell indicated by the yes state information; and
   a video display operably connected to the at least one controller and the video display is operable to display information indicating each holder cell into which medicament is to be loaded.
15. The system of claim 14 wherein the visible information is viewable directly on the holder.

* * * * *

UNITED STATES PATENT AND TRADEMARK OFFICE
CERTIFICATE OF CORRECTION

PATENT NO.        : 9,002,510 B2
APPLICATION NO.   : 13/766092
DATED             : April 7, 2015
INVENTOR(S)       : Duane S. Chudy et al.

It is certified that error appears in the above-identified patent and that said Letters Patent is hereby corrected as shown below:

On the title page
In item 57 ABSTRACT, at line 11 delete "by" and insert --be--.

In the specification
In column 14, line 61, delete "Azithrmycin" and insert --Azithromycin--.
In column 15, line 57, delete "Azithrmycin" and insert --Azithromycin--.
In column 15, line 59, delete "Azithrmycin" and insert --Azithromycin--.
In column 17, line 14, delete "Azithrmycin" and insert --Azithromycin--.
In column 17, line 33, delete "Azithrmycin" and insert --Azithromycin--.
In column 17, line 35, delete "Azithrmycin" and insert --Azithromycin--.

Signed and Sealed this
Seventeenth Day of November, 2015

Michelle K. Lee
*Director of the United States Patent and Trademark Office*